(12) United States Patent
Lee

(10) Patent No.: US 8,158,181 B2
(45) Date of Patent: Apr. 17, 2012

(54) METHOD TO MAKE STEVIOL GLYCOSIDE ISOMERS

(75) Inventor: Thomas Lee, Scarsdale, NY (US)

(73) Assignee: PepsiCo, Inc., Purchase, NY (US)

( * ) Notice: Subject to any disclaimer, the term of this patent is extended or adjusted under 35 U.S.C. 154(b) by 0 days.

(21) Appl. No.: 13/092,534

(22) Filed: Apr. 22, 2011

(65) Prior Publication Data

US 2011/0251381 A1     Oct. 13, 2011

Related U.S. Application Data

(62) Division of application No. 11/856,274, filed on Sep. 17, 2007, now Pat. No. 7,964,232.

(51) Int. Cl.
*A23L 1/236* (2006.01)

(52) U.S. Cl. ................. 426/548; 426/804; 536/18.1

(58) Field of Classification Search .................. None
See application file for complete search history.

(56) References Cited

U.S. PATENT DOCUMENTS 4,404,367 A     9/1983 Stephenson

OTHER PUBLICATIONS

Shin S. Chang and Joanne M. Cook, "Stability Studies of Stevioside and Rebaudioside A. in Carbonated Beverages", J. Agric. Food Chem, 1983, vol. 31, 409-412.
International Search Report and Written Opinion for corresponding PCT/US2008/075192.
M. Kobayashi et al. "Dulcosides A and B, new diterpene glycosides from *Stevia rebaudiana*." Phytochemistry (1977)16: 1405-1408. XP002517591.

J.R. Hanson and B.H. De Oliveira. "The microbiological transformation of steviol derivatives by *Rhizopus stolinifer* and *Gibberella fujikuroi*." Phytochemistry (1990)29: 3805-3807. XP002517592.
I. Prakash et al., "Development of Rebiana, a Natural, Non-Caloric Sweetener." Food and Chemical Toxicology 2008), DOI: 10.1016/j.fct.2008.05.004.
Examination Report dated Nov. 29, 2010, issued from corresponding New Zealand Patent Application No. 583540.
Office Communication dated Dec. 7, 2010, issued from corresponding European Patent Application No. 08799148.5.

(Continued)

*Primary Examiner* — Humera Sheikh
*Assistant Examiner* — Felicia King
(74) *Attorney, Agent, or Firm* — Banner & Witcoff, Ltd.

(57) ABSTRACT

Steviol glycoside isomers are provided having the formula:

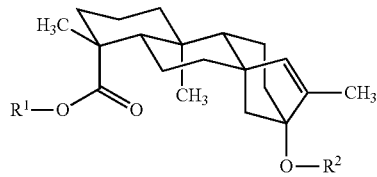

wherein $R^1$ may be 1-β-D-glucopyranosyl or 2-(1-β-D-glucopyranosyl)-1-β-D-glucopyranosyl, and $R^2$ may be hydrogen, 1-β-D-glucopyranosyl, 2-(1-β-D-glucopyranosyl)-1-β-D-glucopyranosyl, 2,3-bis(1-β-D-glucopyranosyl)-1-β-D-glucopyranosyl, 2-(1-α-L-rhamnopyranosyl)-1-β-D-glucopyranosyl, 2-(1-α-L-rhamnopyranosyl)-3-(1-β-D-glucopyranosyl)-1-β-D-glucopyranosyl, or 2-(1-β-D-xylopyranosyl)-3-(1-β-D-glucopyranosyl)-1-β-D-glucopyranosyl. Methods for making steviol glycoside isomers are also disclosed. These compounds may be present in food and beverage products as non-nutritive sweeteners.

20 Claims, 19 Drawing Sheets

Structures of rebaudioside A and iso-rebaudioside A with carbon numbering and relevant bond lengths

OTHER PUBLICATIONS

Examination Report dated Feb. 24, 2011, issued from corresponding Australian Patent Application No. 2008302574.

Official Communication dated Jul. 6, 2011, issued from corresponding Mexican Patent Application No. MX/a/2010/002376.

Bandyukova et al., "Structures of Flavone and Flavanol Glycosides", 1971, Pyatigorsk Pharmaceutical Institute No. 4, pp. 411-423.

Peter Collins, "Dictionary of Carbohydrates", 1998, Chapman & Hall, p. 395.

First Examiner's Report dated Jul. 15, 2011, issued from corresponding Canadian Patent Application No. 2,697,406.

Notice of Preliminary Rejection dated Sep. 1, 2011, issued from corresponding Korean Patent Application No. 10-2010-7005358.

Extended European Search Report dated Nov. 22, 2011, issued from corresponding European Patent Application No. 11007574.4.

Examiner's Report dated Dec. 20, 2011, issued from corresponding Canadian Patent Application No. 2,697,406.

English translation of first Office Action issued for corresponding Chinese Patent Application No. 200880107409.6. This document was provided by the Applicant's foreign associate.

Office Action issued for corresponding Chinese Patent Application No. 200880107409.6, notification date Jan. 31, 2012.

METHOD TO MAKE STEVIOL GLYCOSIDE ISOMERS

PRIORITY CLAIM

This divisional patent application claims priority to U.S. Utility patent application Ser. No. 11/856,274, filed Sep. 17, 2007 now U.S. Pat. No. 7,964,232 and entitled, "Steviol Glycoside Isomers," the entire disclosure of which is hereby incorporated by reference.

FIELD OF THE INVENTION

This invention relates to certain novel isomers of steviol glycosides which are suitable for use as sweeteners, for example, by incorporation into food and beverage products.

BACKGROUND

Due to increasing attention to the negative health effects of obesity in the United States and around the world, market demand for food and beverage products having alternative nutritional characteristics, including, for example, reduced or zero calorie content, has increased as well. There is market demand to replace the high-calorie sweeteners typically used in food and beverage products, such as sucrose and high fructose corn syrup (HFCS), with non-nutritive sweeteners. For example, diet cola beverages have been suggested which are sweetened with potent non-nutritive sweeteners such as steviol glycosides (stevioside, rebaudioside A, etc.).

Steviol glycosides are sweet-tasting compounds extracted from the stevia plant (*Stevia rebaudiana* Berton). Typically, these compounds are found to include stevioside (4-13% dry weight), steviolbioside (trace), the rebaudiosides, including rebaudioside A (1-6%), rebaudioside B (trace), rebaudioside C (1-2%), rebaudioside D (trace), and rebaudioside E (trace), and dulcoside A (0.4-0.7%). Many steviol glycosides are potent, non-nutritive sweeteners. Steviol glycosides comprise a diterpene core (formula I) substituted at $R^1$ and $R^2$ with various combinations of hydrogen, glucose, rhamnose, and xylose.

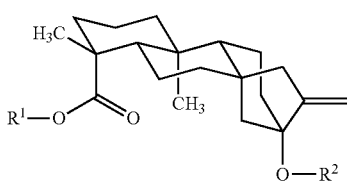

Formula I

For example, $R^1$ may be 1-β-D-glucopyranosyl or 2-(1-β-D-glucopyranosyl)-1-β-D-glucopyranosyl, and $R^2$ may be hydrogen, 1-β-D-glucopyranosyl, 2-(1-β-D-glucopyranosyl)-1-β-D-glucopyranosyl, 2,3-bis(1-β-D-glucopyranosyl)-1-β-D-glucopyranosyl, 2-(1-α-L-rhamnopyranosyl)-1-β-D-glucopyranosyl, 2-(1-α-L-rhamnopyranosyl)-3-(1-β-D-glucopyranosyl)-1-β-D-glucopyranosyl, or 2-(1-β-D-xylopyranosyl)-3-(1-β-D-glucopyranosyl)-1-β-D-glucopyranosyl. Rebaudioside A (wherein $R^1$=1-β-D-glucopyranosyl and $R^2$=2,3-bis(1-β-D-glucopyranosyl)-1-β-D-glucopyranosyl) has a sweetness of about 200 to 300 times the sweetness of sucrose. The food industry has become interested in steviol glycosides in the pursuit of alternative sweeteners. However, the straight replacement of nutritive sweeteners with known potent non-nutritive sweeteners encounters problems of off-tastes, for example slow on-set, or bitter, licorice, or lingering aftertaste. These off-tastes also arise when steviol glycosides are used as non-nutritive sweeteners in food and beverage products. Thus, there is a need for additional alternative non-nutritive sweeteners.

It is therefore an object of at least certain embodiments of the present invention to provide compounds that are useful as sweeteners. It is an object of at least certain embodiments of the invention to provide beverage products or food products having alternative nutritional characteristics and taste properties. These and other objects, features and advantages of the invention or of certain embodiments of the invention will be apparent to those skilled in the art from the following disclosure and description of exemplary embodiments.

BRIEF SUMMARY OF THE INVENTION

A family of new steviol glycoside isomers has now been discovered. In these isomers, the exo-cyclic double bond of formula I has been moved to an endo-cyclic position within the five-membered ring (see Formula II). These compounds are useful as sweeteners, and can be included as such in food and beverage products. In accordance with a first aspect of the invention, a compound is provided having formula II:

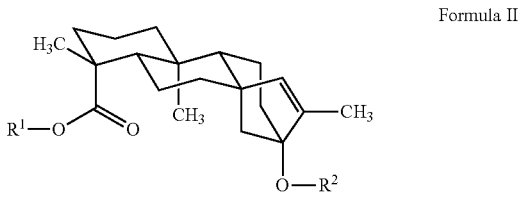

Formula II wherein $R^1$ may be 1-β-D-glucopyranosyl or 2-(1-β-D-glucopyranosyl)-1-β-D-glucopyranosyl, and $R^2$ may be hydrogen, 1-β-D-glucopyranosyl, 2-(1-β-D-glucopyranosyl)-1-β-D-glucopyranosyl, 2,3-bis(1-β-D-glucopyranosyl)-1-β-D-glucopyranosyl, 2-(1-α-L-rhamnopyranosyl)-1-β-D-glucopyranosyl, 2-(1-α-L-rhamnopyranosyl)-3-(1-β-D-glucopyranosyl)-1-β-D-glucopyranosyl, or 2-(1-β-D-xylopyranosyl)-3-(1-β-D-glucopyranosyl)-1-β-D-glucopyranosyl. In certain exemplary embodiments, the compound of formula II may be isolated and purified. As used herein, "isolated and purified" means that the purity of the steviol glycoside isomer is at least 90%.

In accordance with other aspects, a beverage product is provided comprising an aqueous liquid and a compound of formula II.

In accordance with other aspects, a food product is provided comprising a food component and a compound of formula II.

In accordance with another aspect of the invention, a sweetener is provided comprising a compound of formula II.

In accordance with another aspect, a method is provided for preparing the compounds of formula II, comprising the steps of providing an acidic aqueous solution comprising a compound of formula I, and heating the acidic aqueous solution to a temperature within the range of 30° C. to 90° C. for a period of time greater than two days. In certain exemplary embodiments, an acidic aqueous solution comprising rebaudioside A is heated to a temperature within the range of 40° C. to 50° C. at a pH within the range of pH 1.0-4.0 for a period of time greater than two days.

DETAILED DESCRIPTION OF CERTAIN EXEMPLARY EMBODIMENTS

Figure 1:
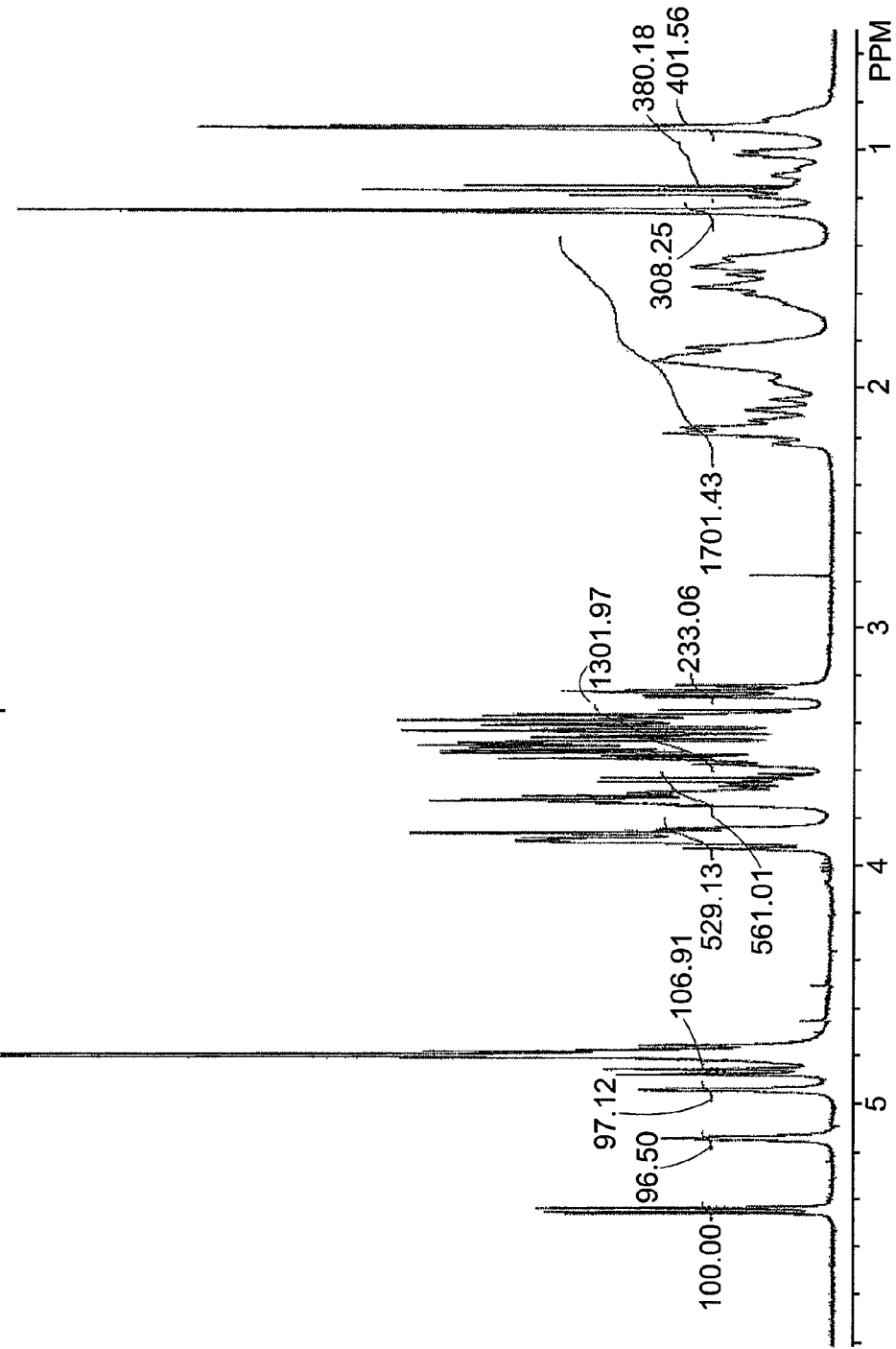
FIG. 1 is a proton NMR spectrum of rebaudioside A.

In certain exemplary embodiments, steviol glycoside isomers of the present invention may be defined by the general formula II:

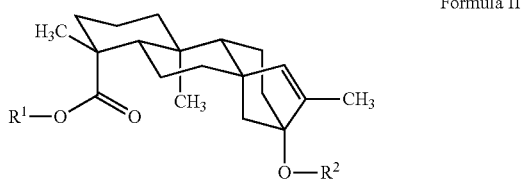

Formula II wherein $R^1$ may 1-β-D-glucopyranosy1 or 2-(1-β-D-glucopyranosyl)-1-β-D-glucopyranosyl, and $R^2$ may be hydrogen, 1-β-D-glucopyranosyl, 2-(1-β-D-glucopyranosyl)-1-β-D-glucopyranosyl, 2,3-bis(1-β-D-glucopyranosyl)-1-β-D-glucopyranosyl, 2-(1-α-L-rhamnopyranosyl)-1-β-D-glucopyranosyl, 2-(1-α-L-rhamnopyranosyl)-3-(1-β-D-glucopyranosyl)-1-β-D-glucopyranosyl, or 2-(1-β-D-xylopyranosyl)-3-(1-β-D-glucopyranosyl)-1-β-D-glucopyranosyl. Certain exemplary embodiments comprise compounds of formula II wherein $R^1$ is 1-β-D-glucopyranosyl and $R^2$ is 2,3-bis(1-β-D-glucopyranosyl)-1-β-D-glucopyranosyl (iso-rebaudioside A), $R^1$ is 1-β-D-glucopyranosyl and $R^2$ is 2-(1-β-D-glucopyranosyl)-1-β-D-glucopyranosyl (iso-stevioside), $R^1$ is 1-β-D-glucopyranosyl and $R^2$ is 1-β-D-glucopyranosyl (iso-rubusoside), $R^1$ is 1-β-D-glucopyranosyl and $R^2$ is 2-(1-α-L-rhamnopyranosyl)-1-β-D-glucopyranosyl (iso-dulcoside A), $R^1$ is 1-β-D-glucopyranosyl and $R^2$ is 2-(1-α-L-rhamnopyranosyl)-3-(1-β-D-glucopyranosyl)-1-β-D-glucopyranose (iso-rebaudioside C), $R^1$ is 2-(1-β-D-glucopyranosyl)-1-β-D-glucopyranosyl and $R^2$ is 2,3-bis(1-β-D-glucopyranosyl)-1-β-D-glucopyranosyl (iso-rebaudioside D), $R^1$ is 2-(1-β-D-glucopyranosyl)-1-β-D-glucopyranosyl and $R^2$ is 2-(1-β-D-glucopyranosyl)-1-β-D-glucopyranosyl (iso-rebaudioside E), $R^1$ is 1-β-D-glucopyranosyl and $R^2$ is 2-(1-β-D-xylopyranosyl)-3-(1-β-D-glucopyranosyl)-1-β-D-glucopyranosyl (iso-rebaudioside F), or $R^1$ is 1-β-D-glucopyranosyl and $R^2$ is hydrogen (iso-steviol II glucosyl ester). One exemplary embodiment comprises the compound of formula II wherein $R^1$ is 1-β-D-glucopyranosyl and $R^2$ is 2,3-bis(1-β-D-glucopyranosyl)-1-β-D-glucopyranosyl. This compound has the structure shown in Formula III below. Hereinafter, this compound is referred to as iso-rebaudioside A

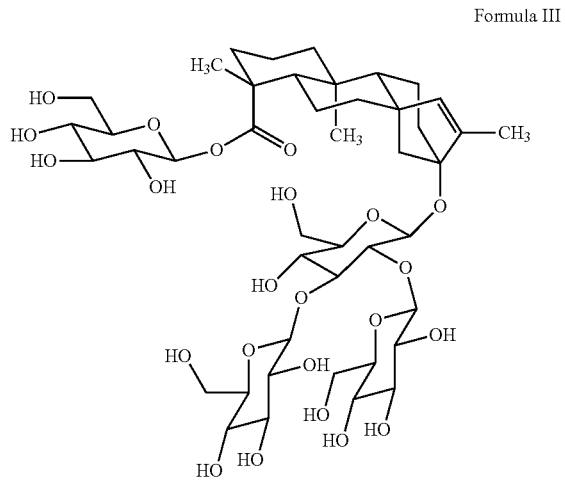

Formula III

In certain exemplary embodiments, steviol glycoside isomers disclosed here may be prepared by heating rebaudioside A in aqueous solution to a temperature within the range of about 30° C. to about 90° C. (e.g., within the range of about 40° C. to about 50° C., such as 43° C.) under strongly acidic conditions (e.g. about pH 1.0-4.0; such as about pH 2.0-2.5) for a sufficient period of time (e.g., greater than two days, such as from two days to about 11 weeks) to produce iso-rebaudioside A (Formula III). A literature report suggests that under acidic conditions (pH 2.4 to 2.6) stevioside or rebaudioside A are quite stable at 60° C., but undergo drastic changes at 100° C., yielding hydrolysis byproducts such as glucose, steviolbioside (from stevioside), rebaudioside B (from rebaudioside A), and unknown compounds which have TLC $R_f$'s or HPLC $t_R$'s very far removed from stevioside or rebaudioside A. When stevioside was subjected to high temperatures, isosteviol was also formed (Formula IV). (S. S. Chang and J. M. Cook, *J. Agric. Food Chem.*, 31, 409-412 (1983)).

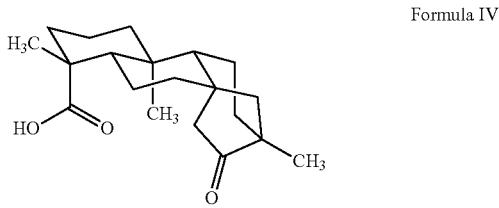

Formula IV

Other literature reports have indicated that the acid-catalyzed hydrolysis of stevioside yields isosteviol (M. Bridel and R. Lavieille, *Journal de Pharmacie et de Chimie*, 14, 321-328, and 369-379 (1931), and J. R. Hanson and B. H. Oliverira, *Natural Product Reports*, 10, 301-309 (1993)). Isosteviol has been shown to be a Wagner-Meerwein rearrangement product involving inversion of the D-ring of steviol (Formula I wherein $R^1$ and $R^2$ each is hydrogen). Literature teachings thus suggest that steviol glycosides, e.g., rebaudioside A, would each undergo an acid-catalyzed isomerization, to a resultant product likewise having isosteviol as the aglycone moiety.

But surprisingly, it has now been found that acid and heat treatment of steviol glycosides, e.g., rebaudioside A, according to the present invention produces steviol glycoside isomers of Formula II, e.g., iso-rebaudioside A (Formula III), which have an aglycone moiety that is neither steviol nor isosteviol, but rather a new aglycone moiety having a migrated double bond in comparison to steviol. The unexpected aglycone moiety of the new compound is hereinafter called iso-steviol II (see Formula II). When $R^1$ and $R^2$ of Formula II are each hydrogen, the compound is called iso-steviol II (Formula V).

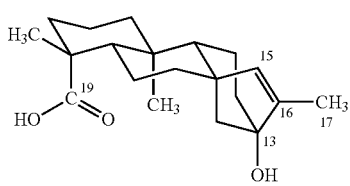

Formula V

In certain exemplary embodiments, steviol glycoside isomers disclosed here may be hydrolyzed to remove glucose, rhamnose, and/or xylose units. Thus, steviol glycoside isomers, e.g., iso-rebaudiosides A-F, iso-stevioside, iso-dulcoside, etc. can be hydrolyzed upon further treatment with heat and acid into various steviol glycoside isomers, e.g., iso-stevioside, iso-rebaudioside B, iso-steviolbioside, iso-rubusoside, iso-steviolmonoside, iso-steviol II glucosyl ester, etc.

In other exemplary embodiments, each of the steviol glycoside isomers disclosed herein may be prepared by treating a suitable steviol glycoside, e.g. the corresponding steviol glycoside, with acid and heat according to the method of invention. Specifically, stevioside may be heated in aqueous solution to a temperature within the range of about 30° C. to about 90° C. (e.g., within the range of about 40° C. to about 50° C., such as 43° C. under strongly acidic conditions (e.g. about pH 1.0-4.0; such as about pH 2.0-2.5) for a sufficient period of time (e.g., greater than two days, such as from two days to about 11 weeks) to produce a compound of formula II wherein $R^1$ is 1-β-D-glucopyranosyl and $R^2$ is 2-(1-β-D-glucopyranosyl)-1-β-D-glucopyranosyl (iso-stevioside). Similarly, rebaudioside B may be heated in aqueous solution to a temperature within the range of about 30° C. to about 90° C. (e.g., within the range of about 40° C. to about 50° C., such as 43° C.) under strongly acidic conditions (e.g. about pH 1.0-4.0; such as about pH 2.0-2.5) for a sufficient period of time (e.g., greater than two days, such as from two days to about 11 weeks) to produce a compound of formula II wherein $R^1$ is hydrogen and $R^2$ is 2,3-bis(1-β-D-glucopyranosyl)-1-β-D-glucopyranosyl (iso-rebaudioside B). Steviolbioside may be heated in aqueous solution to a temperature within the range of about 30° C. to about 90° C. (e.g., within the range of about 40° C. to about 50° C., such as 43° C.) under strongly acidic conditions (e.g. about pH 1.0-4.0; such as about pH 2.0-2.5) for a sufficient period of time (e.g., greater than two days, such as from two days to about 11 weeks) to produce a compound of formula II wherein $R^1$ is hydrogen and $R^2$ is 2-(1-β-D-glucopyranosyl)-1-β-D-glucopyranosyl (iso-steviolbioside). Rubusoside may be heated in aqueous solution to a temperature within the range of about 30° C. to about 90° C. (e.g., within the range of about 40° C. to about 50° C., such as 43° C.) under strongly acidic conditions (e.g. about pH 1.0-4.0; such as about pH 2.0-2.5) for a sufficient period of time (e.g., greater than two days, such as from two days to about 11 weeks) to produce a compound of formula II wherein $R^1$ is 1-β-D-glucopyranosyl and $R^2$ is 1-β-D-glucopyranosyl (iso-rubusoside). Steviolmonoside may be heated in aqueous solution to a temperature within the range of about 30° C. to about 90° C. (e.g., within the range of about 40° C. to about 50° C., such as 43° C.) under strongly acidic conditions (e.g. about pH 1.0-4.0; such as about pH 2.0-2.5) for a sufficient period of time (e.g., greater than two days, such as from two days to about 11 weeks) to produce a compound of formula II wherein $R^1$ is hydrogen and $R^2$ is 1-β-D-glucopyranose (iso-steviolmonoside). Steviol glucose ester (Formula I wherein $R^1$ is 1-β-D-glucopyranosyl and $R^2$ is hydrogen) may be heated in aqueous solution to a temperature within the range of about 30° C. to about 90° C. (e.g., within the range of about 40° C. to about 50° C., such as 43° C.) under strongly acidic conditions (e.g. about pH 1.0-4.0; such as about pH 2.0-2.5) for a sufficient period of time (e.g., greater than two days, such as from two days to about 11 weeks) to produce a compound of formula II wherein $R^1$ is 1-β-D-glucopyranose and $R^2$ is hydrogen (iso-steviol II glucosyl ester). Dulcoside A may be heated in aqueous solution to a temperature within the range of about 30° C. to about 90° C. (e.g., within the range of about 40° C. to about 50° C., such as 43° C.) under strongly acidic conditions (e.g. about pH 1.0-4.0; such as about pH 2.0-2.5) for a sufficient period of time (e.g., greater than two days, such as from two days to about 11 weeks) to produce a compound of formula II wherein $R^1$ is 1-β-D-glucopyranosyl and $R^2$ is 2-(1-α-L-rhamnopyranosyl)-1-β-D-glucopyranosyl (iso-dulcoside A). Rebaudioside C may be heated in aqueous solution to a temperature within the range of about 30° C. to about 90° C. (e.g., within the range of about 40° C. to about 50° C., such as 43° C.) under strongly acidic conditions (e.g. about pH 1.0-4.0; such as about pH 2.0-2.5) for a sufficient period of time (e.g., greater than two days, such as from two days to about 11 weeks) to produce a compound of formula II wherein $R^1$ is 1-β-D-glucopyranosyl and $R^2$ is 2-(1-α-L-rhamnopyranosyl)-3-(1-β-D-glucopyranosyl)-1-β-D-glucopyranose (iso-rebaudioside C). Rebaudioside D may be heated in aqueous solution to a temperature within the range of about 30° C. to about 90° C. (e.g., within the range of about 40° C. to about 50° C., such as 43° C.) under strongly acidic conditions (e.g. about pH 1.0-4.0; such as about pH 2.0-2.5) for a sufficient period of time (e.g., greater than two days, such as from two days to about 11 weeks) to produce a compound of formula II wherein $R^1$ is 2-(1-β-D-glucopyranosyl)-1-β-D-glucopyranosyl and $R^2$ is 2,3-bis(1-β-D-glucopyranosyl)-1-β-D-glucopyranosyl (iso-rebaudioside D). Rebaudioside E may be heated in aqueous solution to a temperature within the range of about 30° C. to about 90° C. (e.g., within the range of about 40° C. to about 50° C., such as 43° C.) under strongly acidic conditions (e.g. about pH 1.0-4.0; such as about pH 2.0-2.5) for a sufficient period of time (e.g., greater than two days, such as from two days to about 11 weeks) to produce a compound of formula II wherein $R^1$ is 2-(1-β-D-glucopyranosyl)-1-β-D-glucopyranosyl and $R^2$ is 2-(1-β-D-glucopyranosyl)-1-β-D-glucopyranosyl (iso-rebaudioside E). Rebaudioside F may be heated in aqueous solution to a temperature within the range of about 30° C. to about 90° C. (e.g., within the range of about 40° C. to about 50° C., such as 43° C.) under strongly acidic conditions (e.g. about pH 1.0-4.0; such as about pH 2.0-2.5) for a sufficient period of time (e.g., greater than two days, such as from two days to about 11 weeks) to produce a compound of formula II wherein $R^1$ is 1-β-D-glucopyranosyl and $R^2$ is 2-(1-β-D-xylopyranosyl)-3-(1-β-D-glucopyranosyl)-1-β-D-glucopyranosyl (iso-rebaudioside F). Other synthesis methods may be employed, for example enzymatic isomerization. Steviol glycoside isomers may be isolated and purified, e.g., by chromatography, recrystallization, etc.

Exemplary acids suitable for use in preparing steviol glycoside isomers under strongly acidic conditions include inorganic acids such as phosphoric acid, hydrochloric acid, nitric acid, sulfuric acid, etc. and/or organic acids such as citric acid, malic acid, tartaric acid, lactic acid, ascorbic acid, etc. One or more acids, and optionally the corresponding acid salt (e.g. citric acid and citrate), are included in the reaction mixture in an amount sufficient to render the reaction mixture strongly acidic (e.g., to achieve a pH value within the range of about pH 1.0-4.0, such as about pH 2.0-2.5). Enzymatic isomerization may also be employed.

Steviol glycosides of Formula I, singularly or as a mixture, can have an additional number of β-D-glucopyranosyl units covalently bonded 4→1 to existing β-D-glucopyranosyl units at $R^1$ and/or $R^2$ via enzymatic transglucosylation reactions with starch, yielding a complex mixture of products. (See Kazuhiro Ohtani and Kazuo Yamasaki, Chapter 7, "Method to improve the taste of the sweet principles of Stevia rebaudiana," p. 145 in the book entitled "Stevia, The genus Stevia", edited by A. Douglas Kinghorn, Taylor & Francis, 2002). These enzyme-modified Stevia extracts are commercially available for use as sweeteners in food and beverage products. Steviol glycoside isomers of Formula II may be subjected to the same kind of enzymatic transglucosylation reactions, yielding a complex mixture of products that are useful as sweeteners for food and beverage products. It is also contemplated that the product of enzymatic transglucosylation of the steviol glycosides of Formula I may be heated in aqueous solution to a temperature within the range of about 30° C. to about 90° C. (e.g., within the range of about 40° C. to about 50° C., such as 43° C.) under strongly acidic conditions (e.g. about pH 1.0-4.0; such as about pH 2.0-2.5) for a sufficient period of time (e.g., greater than two days, such as from two days to about 11 weeks) to produce a complex mixture of products having the aglycone moiety of Formula II. These isomerization products may also be useful as sweeteners in food and beverage products.

In certain exemplary embodiments, steviol glycoside isomers comprising at least one compound of Formula II may be used as a potent non-nutritive sweetener. Sweeteners are edible consumables suitable for consumption and for use in foods and beverages. As used herein, "edible consumables" means a food or beverage or an ingredient of a food or beverage for human or animal consumption. As used herein, a "non-nutritive sweetener" is one which does not provide significant caloric content in typical usage amounts, e.g., one which imparts less than 5 calories per 8 oz. serving of beverage to achieve the sweetness equivalent of 10 Brix of sugar. As used herein, a "potent sweetener" means a sweetener which is at least twice as sweet as sugar (sucrose), that is, a sweetener which on a weight basis requires no more than half the weight of sugar to achieve an equivalent sweetness. For example, a potent sweetener may require less than one-half the weight of sugar to achieve an equivalent sweetness in a beverage sweetened to a level of 10 degrees Brix with sugar.

In certain exemplary embodiments, a sweetener may comprise at least one compound of formula II, and optionally a filler, a bulking agent such as dextrose, maltodextrin, erythritol, tagatose, or erythritol and tagatose blend, polydextrose, and/or an anti-caking agent.

In certain exemplary embodiments, one or more of the steviol glycoside isomers disclosed here may be present as a non-nutritive sweetener in a beverage product. Exemplary beverage products comprise an aqueous liquid and a compound of formula II, and include beverages such as, for example, ready to drink liquid formulations, beverage concentrates and the like. Beverages include, e.g., carbonated and non-carbonated soft drinks, fountain beverages, frozen ready-to-drink beverages, frozen carbonated beverages, liquid concentrates, powdered concentrates, coffee beverages, tea beverages, dairy beverages, flavored waters, enhanced waters, fruit juice, fruit juice-flavored drinks, fruit-flavored drinks, sports drinks, soy drinks, vegetable drinks, grain-based drinks (e.g. malt beverages), fermented drinks (e.g., yogurt and kefir), alcoholic beverages, and mixtures of any of them. Exemplary fruit juice sources include citrus fruit, e.g. orange, grapefruit, lemon and lime, berry, e.g. cranberry, raspberry, blueberry and strawberry, apple, grape, pineapple, prune, pear, peach, cherry, mango, and pomegranate. Beverage products include bottle, can, and carton products and fountain syrup applications.

The terms "beverage concentrate" and "syrup" are used interchangeably throughout this disclosure. At least certain exemplary embodiments of the beverage concentrates contemplated are prepared with an initial volume of water to which the additional ingredients are added. Full strength beverage compositions can be formed from the beverage concentrate by adding further volumes of water to the concentrate. Typically, for example, full strength beverages can be prepared from the concentrates by combining approximately 1 part concentrate with between approximately 3 to approximately 7 parts water. In certain exemplary embodiments the full strength beverage is prepared by combining 1 part concentrate with 5 parts water. In certain exemplary embodiments the additional water used to form the full strength beverages is carbonated water. In certain other embodiments, a full strength beverage is directly prepared without the formation of a concentrate and subsequent dilution.

In certain exemplary embodiments, one or more of the steviol glycoside isomers disclosed here may be present as a non-nutritive sweetener in a food product. Food products comprise at least one food component, i.e., any edible material suitable for human or animal consumption, whether or not fully or partially digestible. Non-limiting examples of food components include proteins, carbohydrates, fats, vitamins, minerals, etc. Food products comprising a compound of formula II disclosed here include, e.g., oatmeal, cereal, baked goods (e.g., cookies, crackers, cakes, brownies, breads, etc.), snack foods (e.g., potato chips, tortilla chips, popcorn, snack bars, rice cakes, etc.), and other grain-based food products. All variations, alternatives, options, etc., discussed elsewhere in this disclosure apply to food embodiments of the invention.

It should be understood that food or beverage products in accordance with this disclosure may have any of numerous different specific formulations or constitutions. The formulation of a food or beverage product in accordance with this disclosure can vary to a certain extent, depending upon such factors as the product's intended market segment, its desired nutritional characteristics, flavor profile and the like. For example, it will generally be an option to add further ingredients to the formulation of a particular food or beverage embodiment, including any of the food or beverage formulations described herein. Additional (i.e., more and/or other) sweeteners may be added. Acidulants, flavorings, colorings, electrolytes, minerals, non-mineral nutritional supplements, fruit juices or other fruit products, tastents, masking agents and the like, flavor enhancers, buffering agents, thickeners, emulsifiers, edible particulates, anti-foaming agents, preservatives, carbonation, and mixtures thereof typically can be added to any such formulations to vary the taste, mouthfeel, nutritional characteristics, functionality, etc. of the food or beverage product. Examples of non-mineral nutritional supplement ingredients are known to those of ordinary skill in the art and include, for example, antioxidants and vitamins, including Vitamins A, D, E (tocopherol), C (ascorbic acid), B (thiamine), $B_2$ (riboflavin), $B_6$, $B_{12}$, and K, niacin, folic acid, biotin, and combinations thereof The optional non-mineral nutritional supplements are typically present in amounts generally accepted under good manufacturing practices. Exemplary amounts are between about 1% and about 100% RDV (recommended daily value), where such RDV are established. In certain exemplary embodiments the non-mineral nutritional supplement ingredient(s) are present in an amount of from about 5% to about 20% RDV, where established. Additional and alternative suitable ingredients will be recognized by those skilled in the art given the benefit of this disclosure.

Certain exemplary embodiments of carbonated beverages disclosed here are cola flavored carbonated beverages, which characteristically comprise carbonated water, a compound of formula II, kola nut extract and/or other cola flavoring, caramel coloring, an acidulant (e.g. phosphoric acid), and optionally other ingredients such as other sweeteners. Certain other exemplary embodiments of carbonated beverages disclosed here are citrus flavored (e.g., lemon-lime, grapefruit, lemon, lime, etc.) carbonated beverages, which characteristically comprise carbonated water, a compound of formula II, citrus flavoring, an acidulant (e.g. citric acid), and optionally other ingredients such as coloring agents and/or other sweeteners. In certain exemplary embodiments, a beverage concentrate is provided comprising water, a compound of formula II, cola flavoring, caramel coloring, and acidulant (e.g., phosphoric acid), and optionally other ingredients such as other sweeteners. In certain exemplary embodiments, a beverage concentrate is provided comprising water, a compound of formula II, citrus flavoring, an acidulant (e.g., citric acid), and optionally other ingredients such as coloring agents and/or other sweeteners.

In at least certain exemplary embodiments of the food and beverage products disclosed herein, additional/other sweeteners may be included, for example, nutritive sweeteners or non-nutritive sweeteners. Non-limiting examples of nutritive sweeteners include sucrose, liquid sucrose, fructose, liquid fructose, glucose, liquid glucose, glucose-fructose syrup from natural sources such as apple, chicory, agave, honey, etc., e.g., high fructose corn syrup, chicory syrup, Agave syrup, invert sugar, medium invert sugar, maple syrup, maple sugar, honey, brown sugar molasses, e.g., cane molasses and sugar beet molasses, sorghum syrup, an mixtures of any of them. Such sweeteners are present in at least certain exemplary embodiments in an amount of from about 0.1% to about 20% by weight of the finished food or beverage product, such as from about 6% to about 16% by weight, depending upon the desired level of sweetness for the finished food or beverage product. Nutritive sweeteners may be present in beverage concentrate embodiments up to about 60% by weight of the beverage concentrate.

Non-limiting examples of potent non-nutritive natural sweeteners that may be included in food and beverage products include rebaudioside A, stevioside, other steviol glycosides, Stevia rebaudiana extracts, Lo Han Guo (LHG), e.g., LHG juice concentrate or LHG powder, thaumatin, monellin, brazzein, monatin, and mixtures of any of them. LHG, if used, may have for example, mogroside V content of from about 2 to about 99%. In certain exemplary embodiments, a food or beverage product is provided which comprises a mixture of a compound of formula II and LHG having a mogroside V content of at least 30%. In certain exemplary embodiments, the LHG in the mixture has a mogroside V content of about 45%, plus or minus 5%. In certain exemplary embodiment, a mixture comprising LHG and a compound of formula II provides at least 10% of the sweetness in a food or beverage product. In certain exemplary embodiments, the mixture provides about ⅓ to about ⅔ of the sweetness. Other examples of non-nutritive sweeteners include sorbitol, mannitol, xylitol, glycyrrhizin, maltitol, maltose, lactose, xylose, arabinose, isomalt, lactitol, trehalulose, ribose, fructo-oligosaccharides, and mixtures of any of them. Optionally, the sweetener component can include erythritol, tagatose, an erythritol and tagatose blend, or polydextrose. In certain exemplary embodiments, a food or beverage product is provided which comprises a compound of formula II and either erythritol, tagatose, or a blend of erythritol and tagatose.

Non-limiting examples of potent non-nutritive artificial sweeteners that may be included in food and beverage products include peptide based sweeteners, e.g., aspartame, neotame, and alitame, and non-peptide based sweeteners, e.g., sodium saccharin, calcium saccharin, acesulfame (including but not limited to acesulfame potassium), cyclamate (including but not limited to sodium cyclamate and/or calcium cyclamate), neohesperidin dihydrochalcone, sucralose, and mixtures of any of them. Potent non-nutritive sweeteners typically are employed at a level of milligrams per ounce of food or beverage according to their sweetening power, any applicable regulatory provisions of the country where the food or beverage is to be marketed, the desired level of sweetness of the food or beverage, etc. Mixtures of any of the above nutritive and non-nutritive sweeteners are included within the scope of the disclosed invention. It will be within the ability of those skilled in the art, given the benefit of this disclosure, to select suitable additional or alternative sweeteners for use in various embodiments of the food and beverage products disclosed here.

Those of ordinary skill in the art will understand that, for convenience, some ingredients are described here in certain cases by reference to the original form of the ingredient in which it is added to the beverage product formulation. Such original form may differ from the form in which the ingredient is found in the finished food or beverage product. Thus, for example, in certain exemplary embodiments of the cola beverage products of this disclosure, sucrose and liquid sucrose would typically be substantially homogenously dissolved and dispersed in the beverage. Likewise, other ingredients identified as a solid, concentrate (e.g., juice concentrate), etc. would typically be homogenously dispersed throughout the food or beverage product, rather than remaining in their original form. Thus, reference to the form of an ingredient of a food or beverage product formulation should not be taken as a limitation on the form of the ingredient in the food or beverage product, but rather as a convenient means of describing the ingredient as an isolated component of the product formulation.

In at least certain exemplary embodiments, food and beverage products disclosed here may be preserved by pasteurization. The pasteurization process may include, for example, ultra high temperature (UHT) treatment and/or high temperature-short time (HTST) treatment. The UHT treatment includes subjecting the food or beverage product to high temperatures, such as by direct steam injection or steam infusion, or by indirect heating in a heat exchanger. Generally, after the product is pasteurized, the product can be cooled as required by the particular product composition/configuration and/or the package filling application. For example, in one embodiment, the food or beverage product is subjected to heating to about 85° C. to about 121° C. for a short period of time, for example, about 1 to 60 seconds, then cooled quickly to about 2.2° C.+/−2.8° C.) for refrigerated products, to ambient temperature for shelf stable or refrigerated products, and to about 85° C.+/−5.5° C. for hot-fill applications for shelf-stable products. The pasteurization process is typically conducted in a closed system, so as not to expose the food or beverage product to atmosphere or other possible sources of contamination. Other pasteurization or sterilization techniques may also be useful, such as, for example, aseptic packaging, tunnel pasteurization, or retort processing. In general, tunnel pasteurization methods typically use lower temperatures for a longer time, e.g., about 71° C. for 10-15 minutes, and retort methods typically use, e.g., about 121° C. for 3-5 minutes at elevated pressure, i.e., at pressure above 1 atmosphere. In addition, multiple pasteurization processes may be carried out in series or parallel, as necessitated by the food or beverage product or ingredients.

The following examples are specific embodiments of the present invention but are not intended to limit it.

Example 1

Synthesis of iso-rebaudioside A: Rebaudioside A (0.5 g) dissolved in an aqueous citrate buffer solution (about pH 2.0) was heated for 10 weeks at about 43.3° C. The reaction mixture was then freeze-dried and then subjected to a silica gel column (1×20 cm) eluting with a solvent system of 70% acetone, 15% triethylamine, and 15% water. Two fractions were isolated, with fraction 2 containing rebaudioside A and iso-rebaudioside A. After concentration, approximately 6 mg of oil was isolated from fraction 2. The oil was dissolved in $D_2O$ (0.6 mL) and left at room temperature for about three days. Clear, colorless needle crystals (1-2 mg) formed and were isolated for analysis.

Example 2

Figure 2:
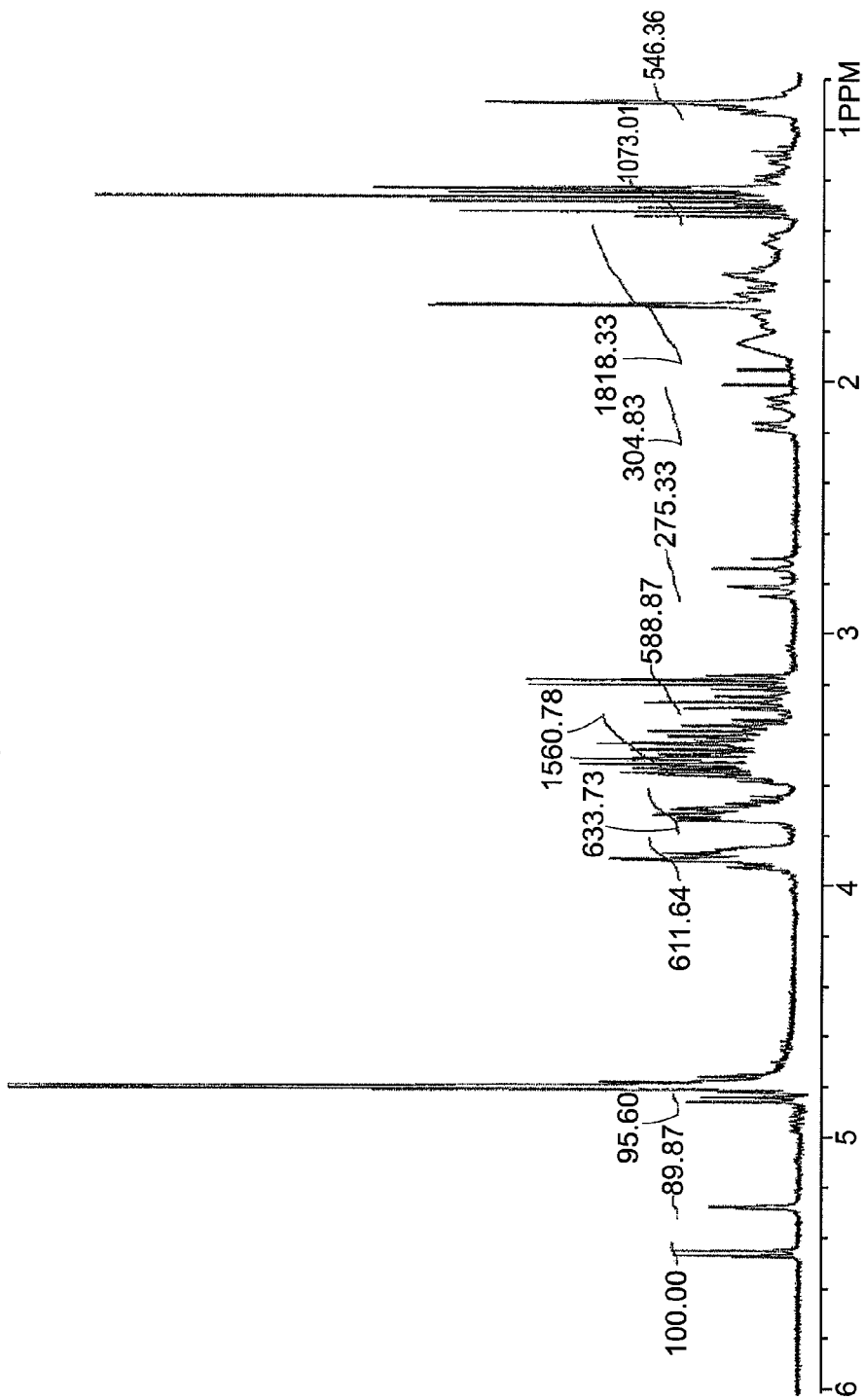
FIG. 2 is a proton NMR spectrum of iso-rebaudioside A.
Figure 3:
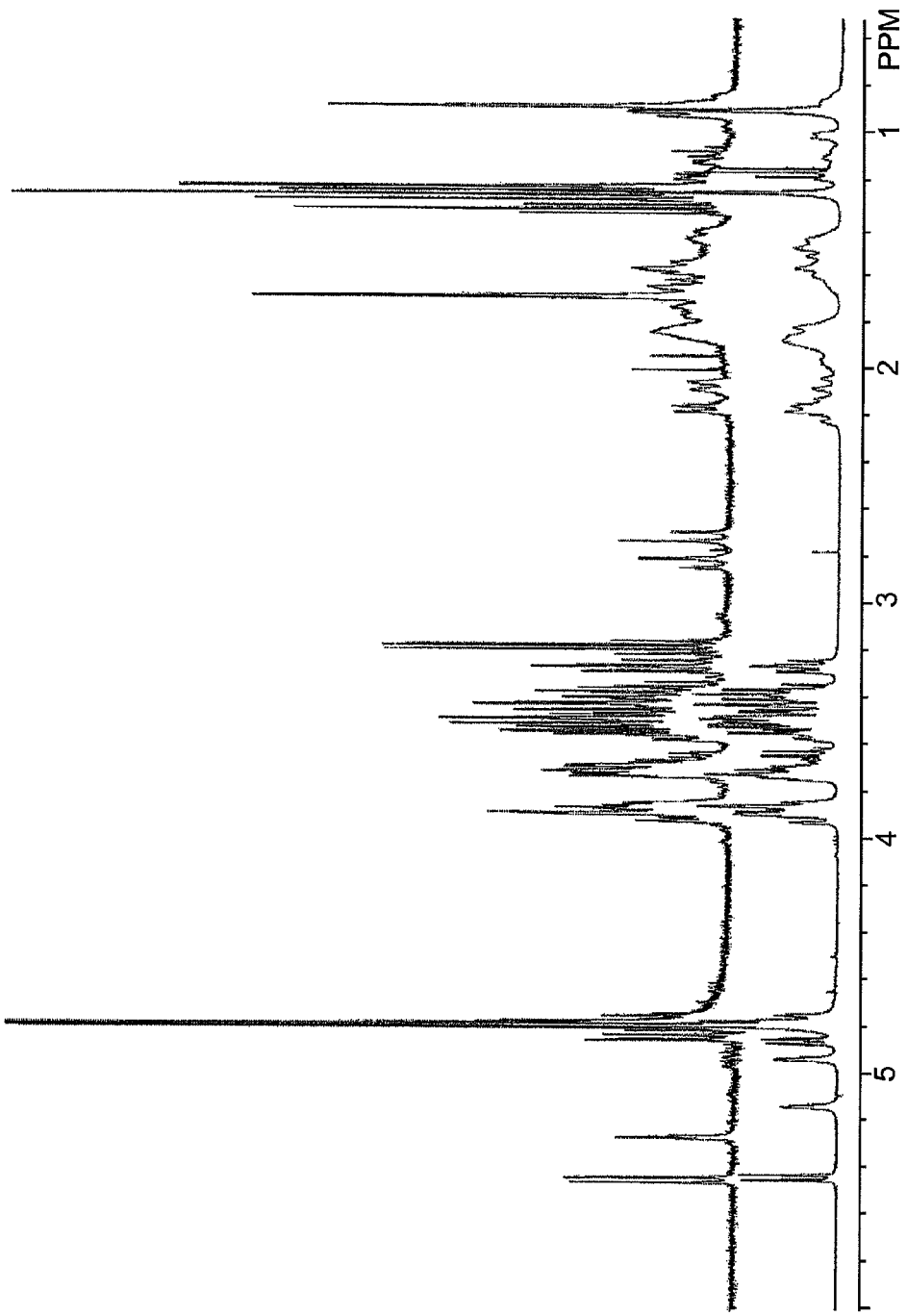
FIG. 3 is an overlay of the spectra from FIGS. 1 and 2.

Analysis of Iso-Rebaudioside A:

A small amount of the crystalline product of Example 1 was analyzed by proton NMR and compared to the parent rebaudioside A spectrum ($D_2O$, 400 MHz $^1$H-NMR). The two compounds were not identical, which showed that a new isomer had formed. FIGS. 1 and 2 contain the proton NMR spectra of a rebaudioside A standard and iso-rebaudioside A, respectively. FIG. 3 shows an overlay of the two spectra.

Figure 4:
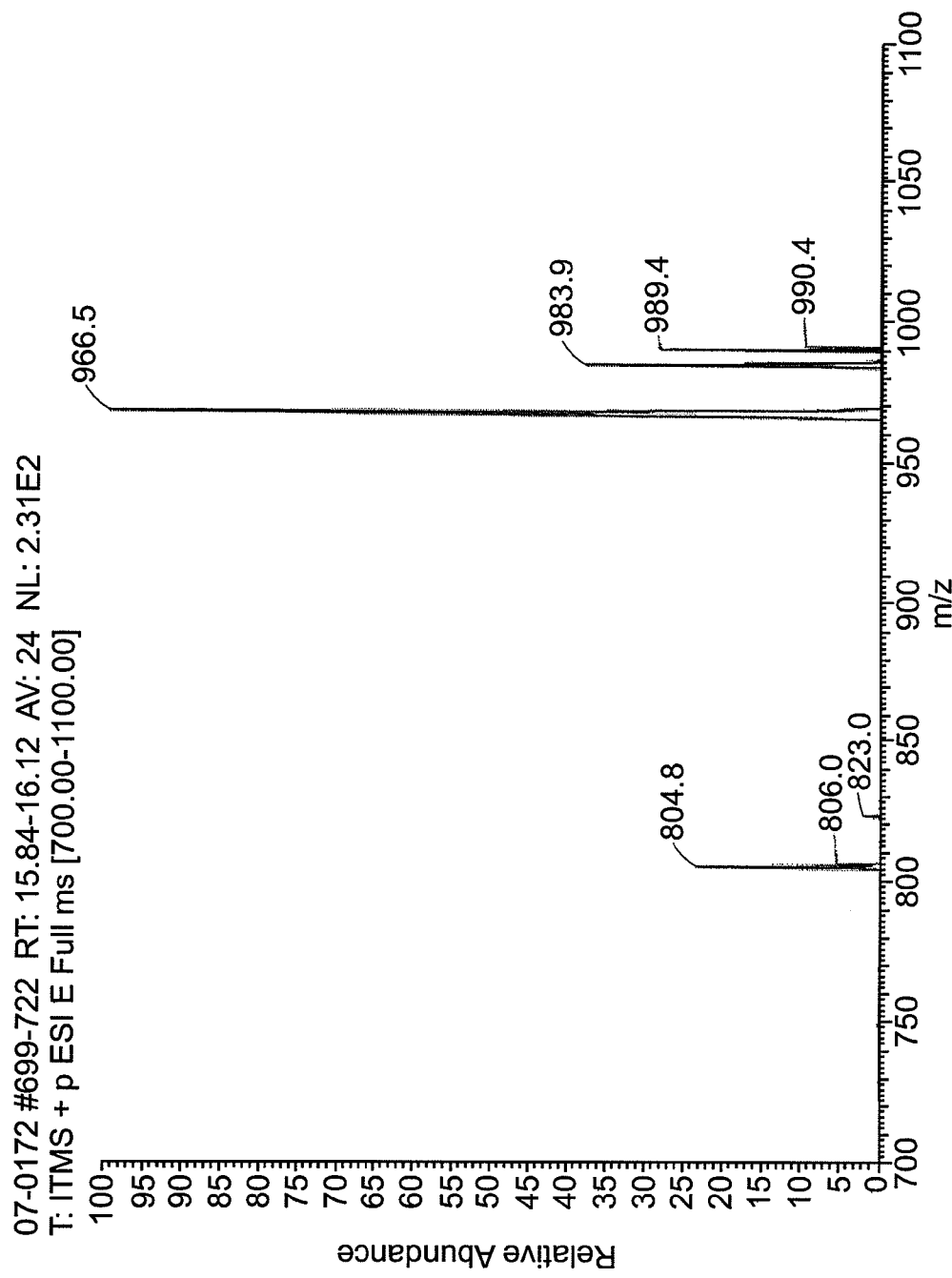
FIG. 4 is an ESI mass spectrum of rebaudioside A.
Figure 5:
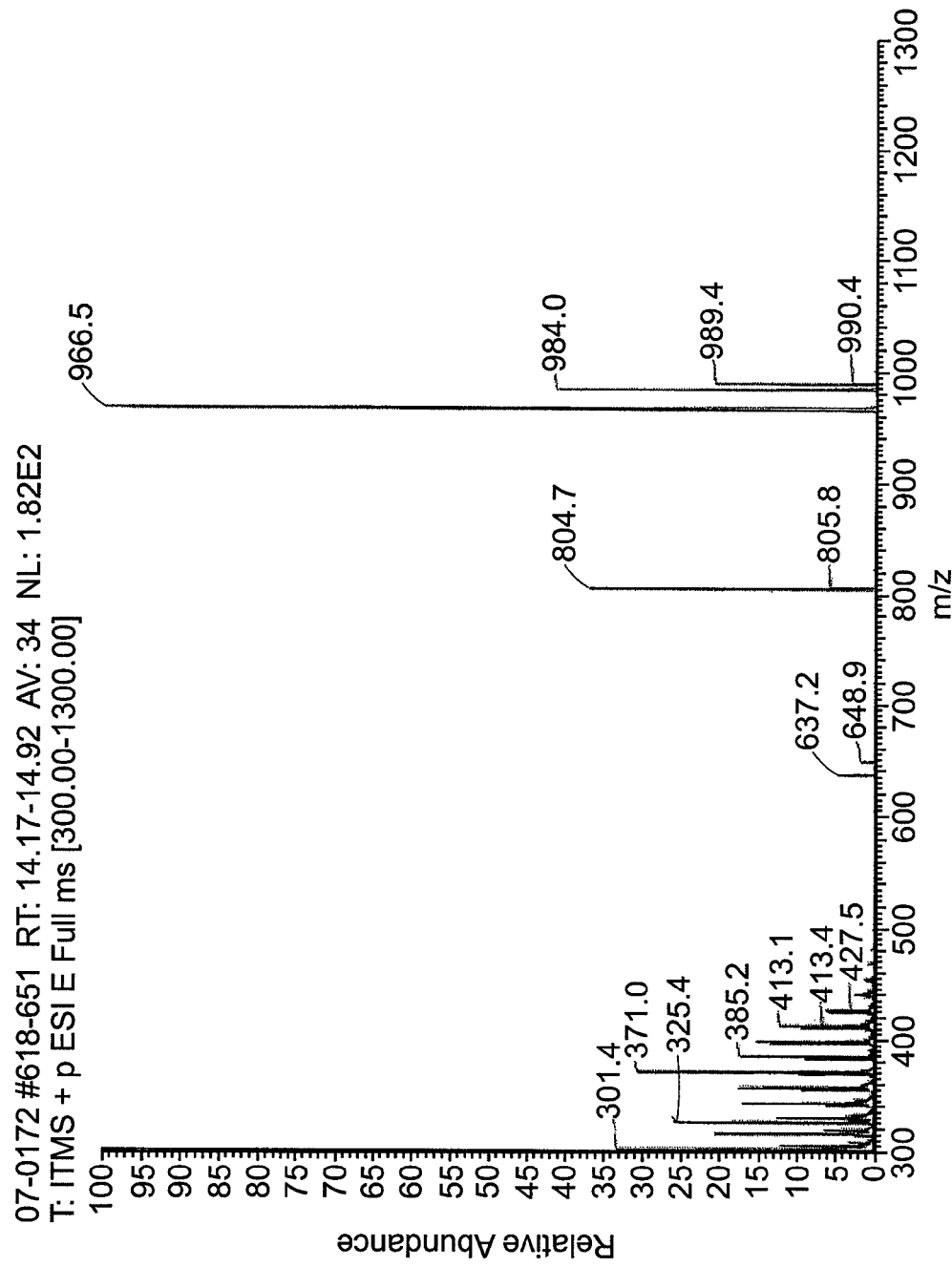
FIG. 5 is an ESI mass spectrum of iso-rebaudioside A.

Samples of rebaudioside A standard and the crystalline product of Example 1 were submitted for mass spectral analysis (ESI positive ion mode). Both compounds showed the expected molecular weight for rebaudioside A of 966.5 amu and similar fragmentation patterns. FIGS. 4 and 5 show the mass spectra of rebaudioside A and iso-rebaudioside A, respectively.

Analyses were performed on a C-18 reverse-phase analytical column (Alltima 2.1×250 mm) at a flow rate of 0.250 mL/min with detection at 210 nm, and evaporative light scattering (ELSD) detection. The column was pre-quilibrated with water containing 0.1% trifluoroacetic acid (solvent A). Solvent B was acetonitrile containing 0.1% trifluoroacetic acid. The gradient conditions were:

| Time (min) | Solvent A % | Solvent B % |
|---|---|---|
| 0 | 100 | 0 |
| 3 | 100 | 0 |
| 35 | 5 | 95 |
| 40 | 5 | 95 |
| 41 | 0 | 00 |
| 50 | 0 | 100 |

The product of Example 1 was injected in water (5 µL), resulting in two peaks in a 30:70 ratio that were not baseline resolved, the minor peak eluting at 22.523 minutes and the major peak eluting at 22.680 minutes. A rebaudioside A standard was run on the HPLC under the same conditions and proved to be the peak eluting at 22.523 min. The same rebaudioside A standard was enriched with a small amount of the crystalline product of Example 1, and when run on the HPLC revealed a proportionally increased peak area at 22.680 minutes.

Figure 6:
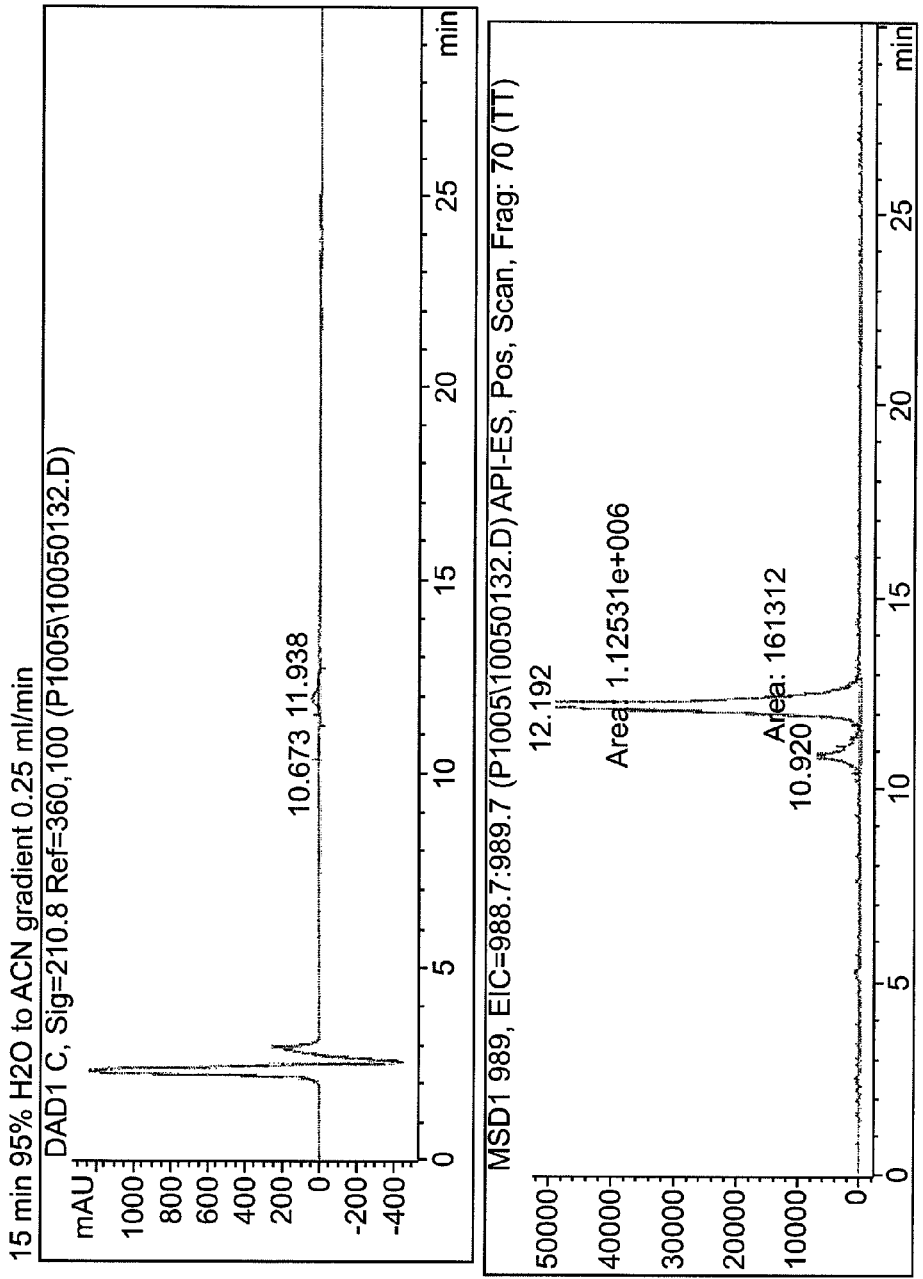
FIG. 6 is an HPLC chromatogram of a 10-week reaction mixture containing rebaudioside A and iso-rebaudioside A.
Figure 7:
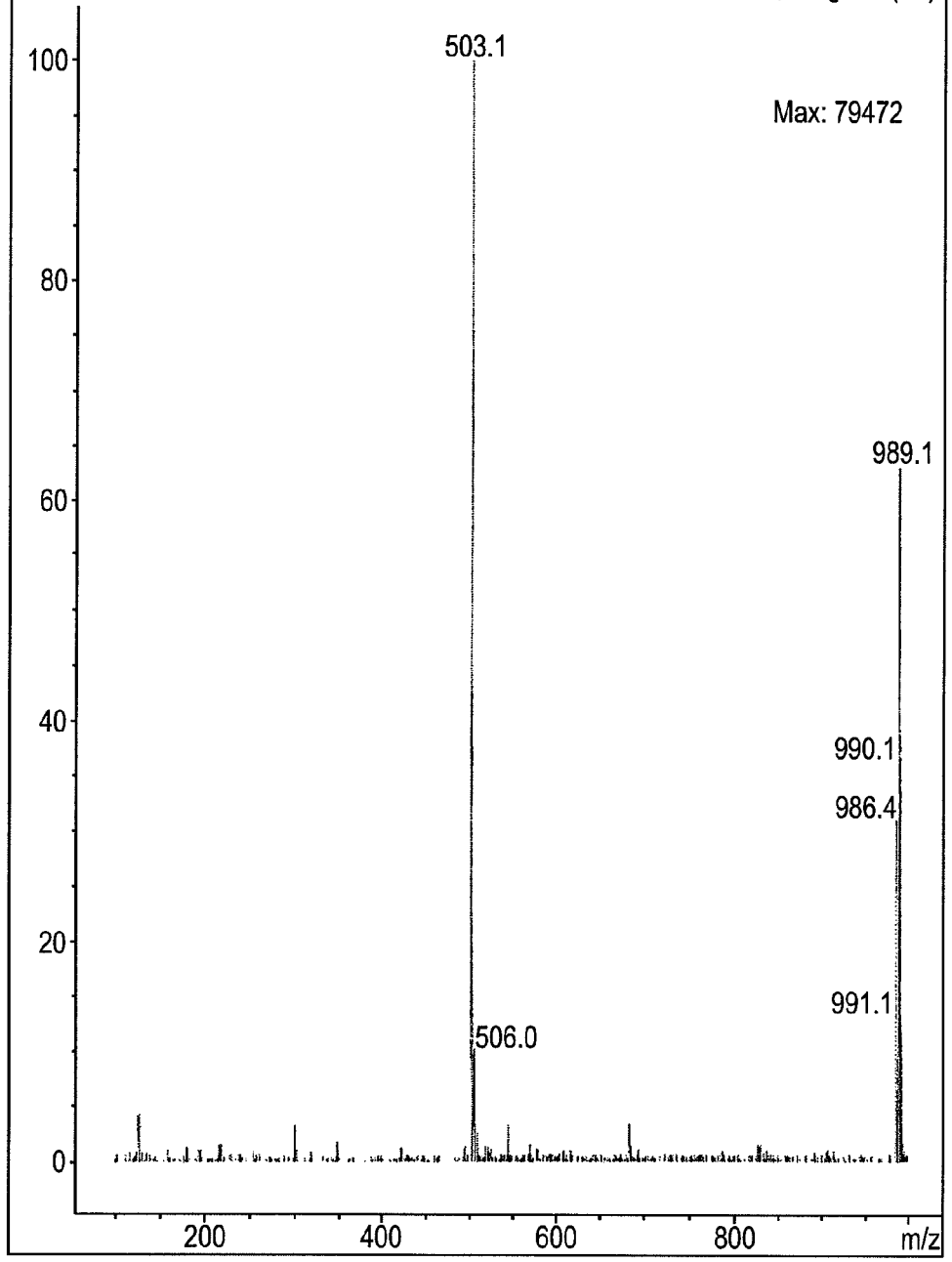
FIG. 7 is an ESI mass spectrum of the iso-rebaudioside A peak from FIG. 6.
Figure 8:
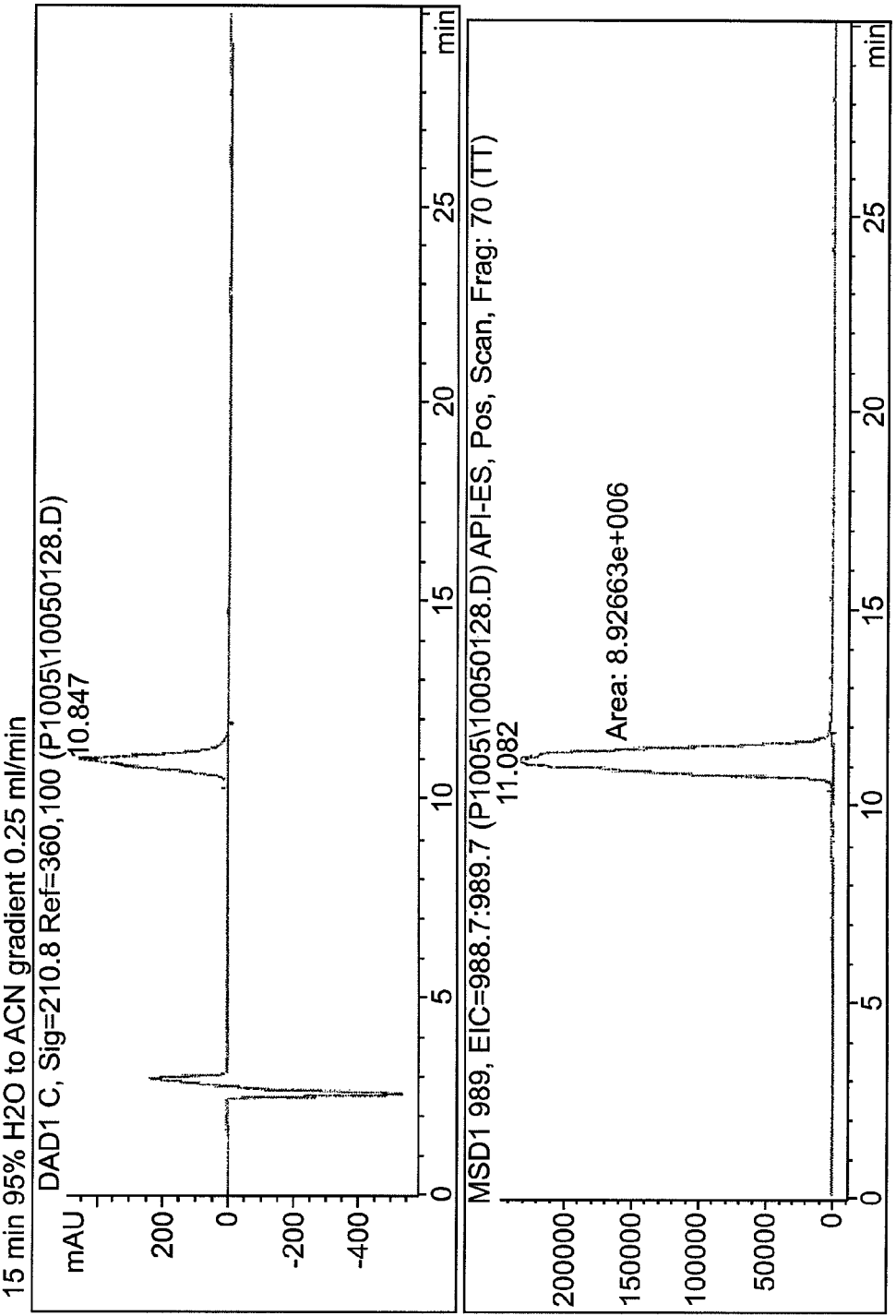
FIG. 8 is an HPLC chromatogram of rebaudioside A.
Figure 9:
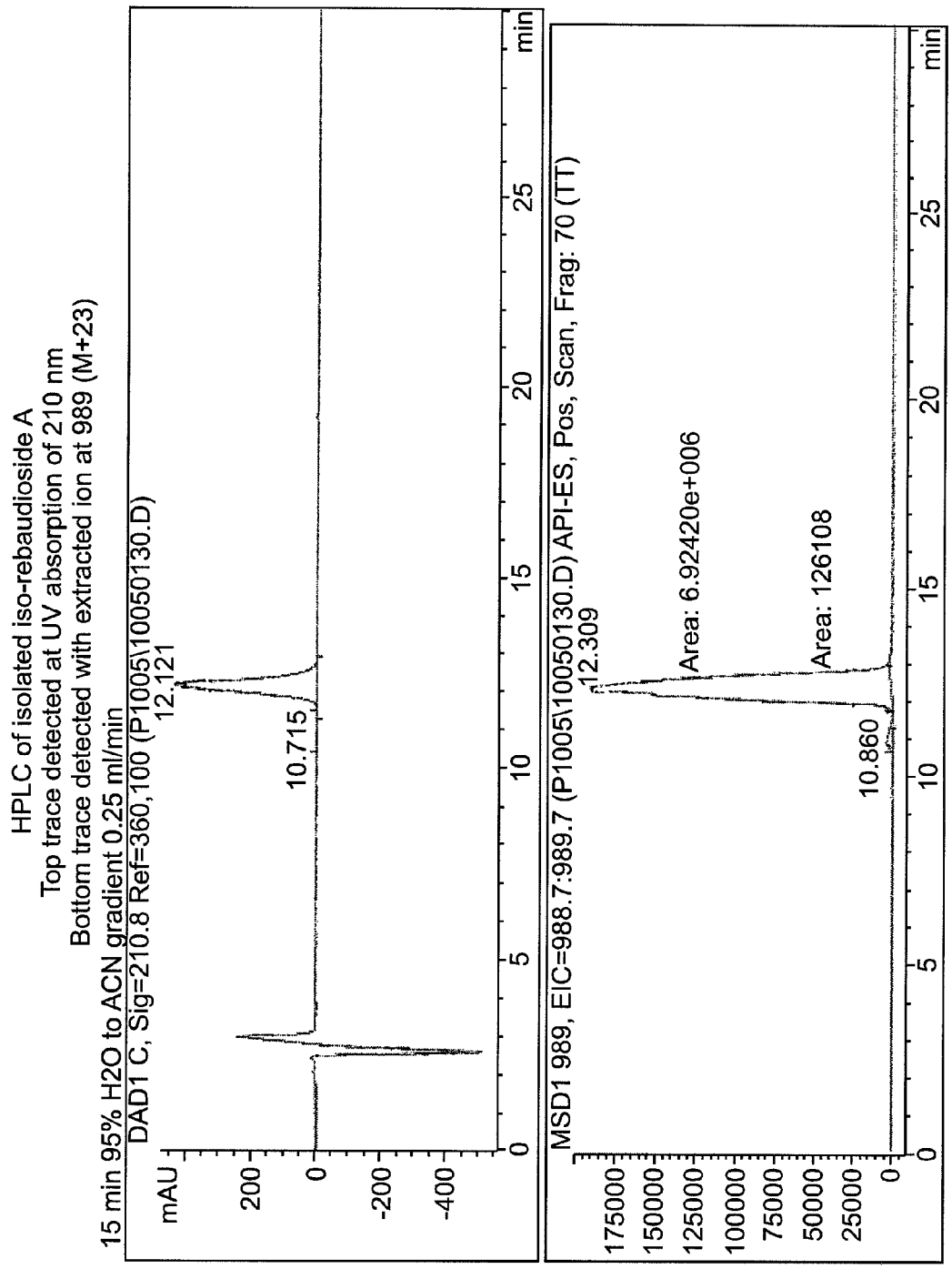
FIG. 9 is an HPLC chromatogram of iso-rebaudioside A.
Figure 10:
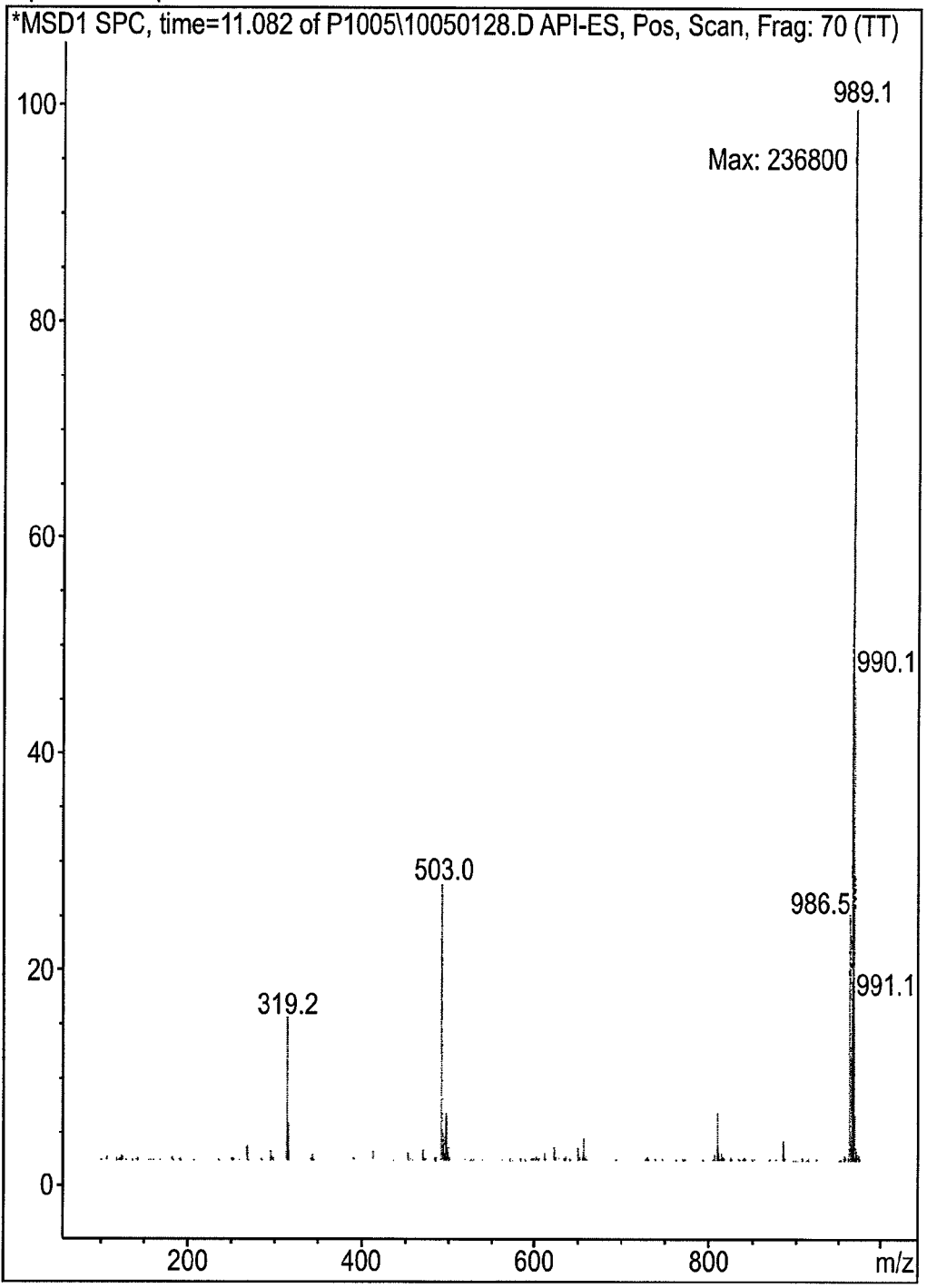
FIG. 10 is ESI mass spectrum of the rebaudioside A peak from FIG. 8.
Figure 11:
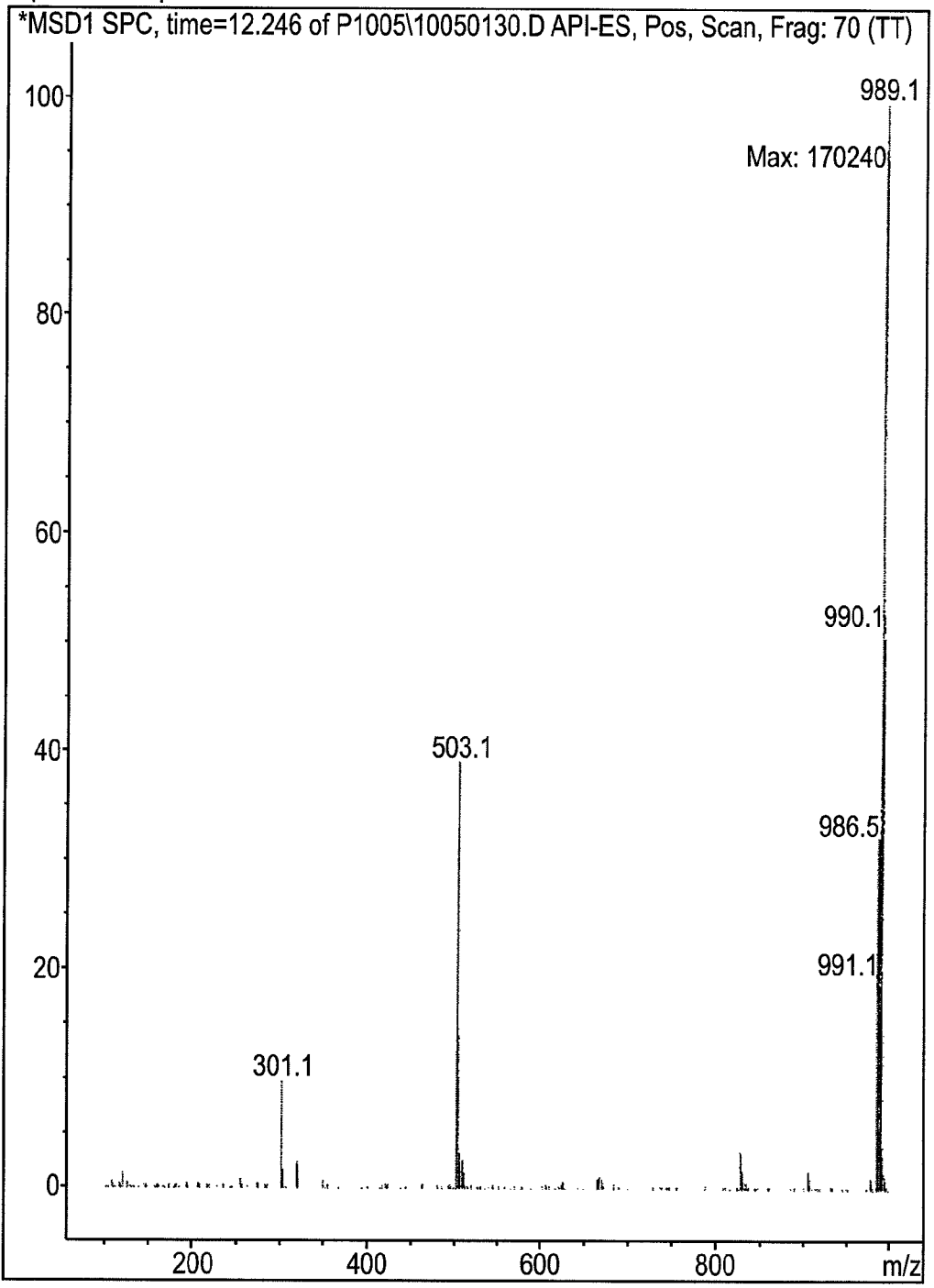
FIG. 11 is ESI mass spectrum of the iso-rebaudioside A peak from FIG. 9.
Figure 12:
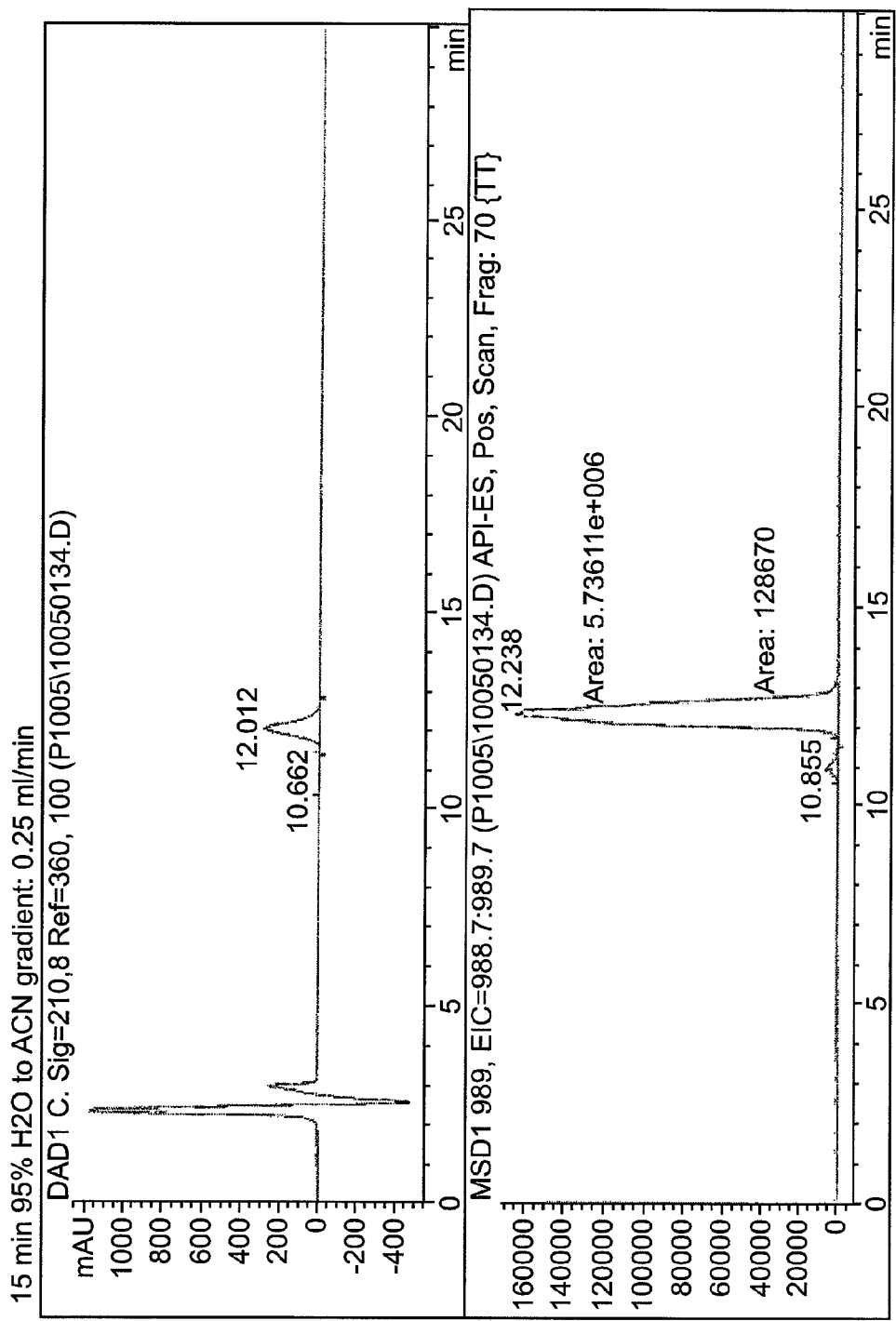
FIG. 12 is an HPLC chromatogram of a 10-week reaction mixture enriched with isolated iso-rebaudioside A.
Figure 13:
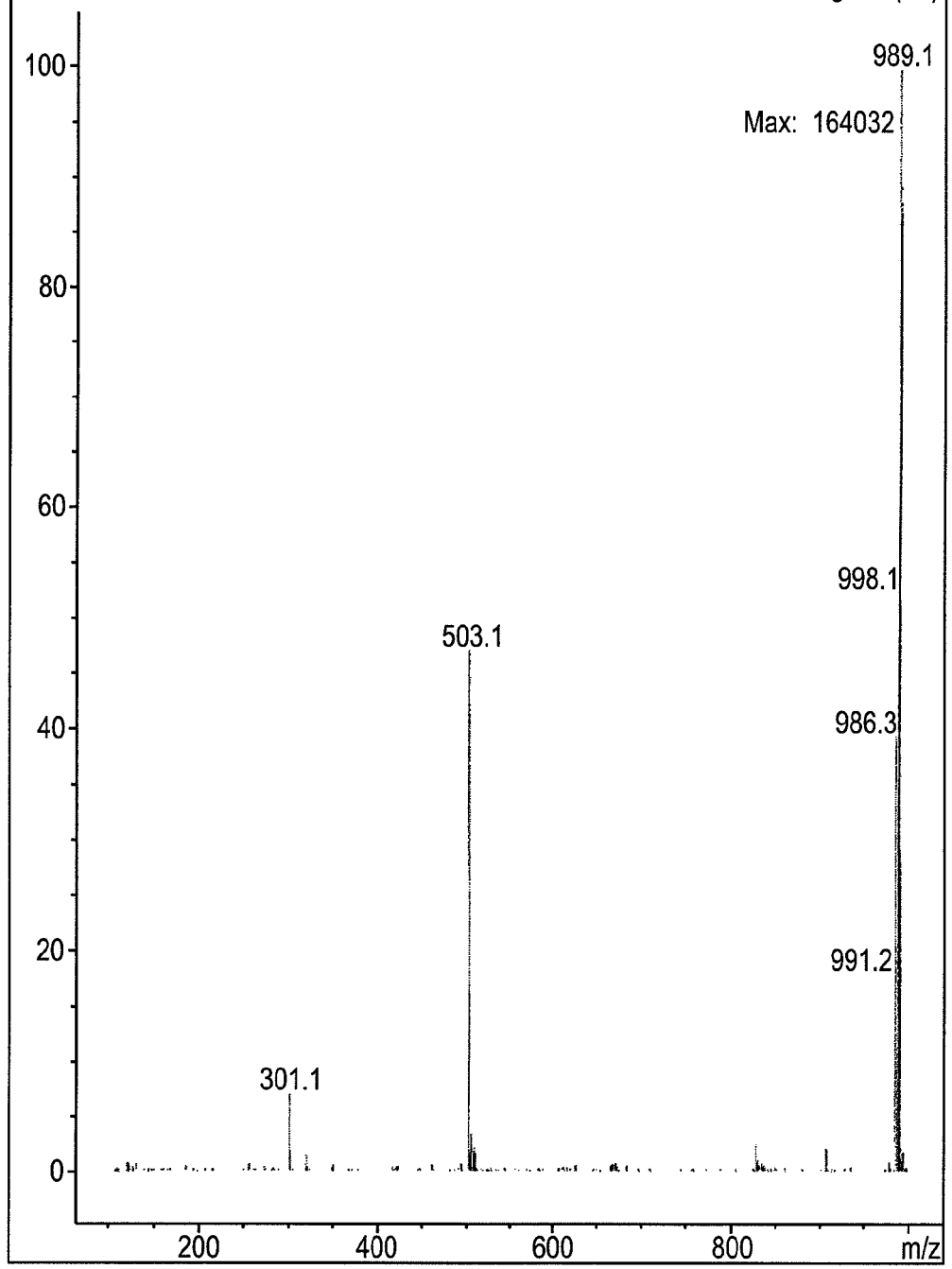
FIG. 13 is ESI mass spectrum of the iso-rebaudioside A peak from FIG. 12.

Rebaudioside A and its isomer were baseline resolved by injecting the crude 10 week reaction mixture of Example 1 onto the same C-18 reverse-phase column, eluting with an isocratic mixture consisting of 30:70 acetonitrile:water with 0.1% formic acid, at a flow rate of 0.25 mL/min. Baseline resolution was also obtained using a 15 minute gradient of 95% water to acetonitrile at a flow rate of 0.25 mL/min. Under these conditions, rebaudioside A eluted at about 10.9 minutes, and iso-rebaudioside A eluted at about 12.2 minutes (FIG. 6). Detection by LC/MS (ESI-MS) exhibited a molecular ion of 989 (M+23, the Na ion adduct) for the iso-rebaudioside A peak at 12.2 minutes (FIG. 7). A rebaudioside A standard and isolated iso-rebaudioside A were analyzed separately by LC/MS. The rebaudioside A standard eluted at 11.08 minutes (FIG. 8), corresponding to the 10.9 minute peak in FIG. 6, and the isolated iso-rebaudioside A eluted at 12.1 minutes (FIG. 9), corresponding to the 12.2 minute peak in FIG. 6. Both the standard and the isolated product had a molecular ion of 989 (FIGS. 10 and 11, respectively). A mixture of crude 10 week reaction mixture from Example 1 enriched with isolated iso-rebaudioside A was analyzed by LC/MS. The added iso-rebaudioside A co-eluted with and increased the area of the peak at 12.2 minutes (FIG. 12, compare with FIG. 6), and mass spectrum of the 12.2 minute peak still gave a molecular ion of 989 (FIG. 13).

The NMR, HPLC, and mass spectral data together unambiguously confirmed that the new compound iso-rebaudioside A was a chemically distinct derivative of rebaudioside A.

Example 3

Synthesis of iso-rebaudioside A: Rebaudioside A (5 g) was dissolved in an aqueous solution of citrate buffer (pH 2, 100 mM, 200 mL) and heated to about 75° C. The reaction progress was monitored via HPLC and when the ratio of iso-rebaudioside A to rebaudioside A was greater than 75% (72 hours) the reaction mixture was evaporated to a sticky crystalline solid. The product mixture was passed through a silica column (10×40 cm) eluting with acetone:water:triethylamine (70:15:15) to provide a glassy oil (about 1.0 g). Analysis by HPLC showed the presence of rebaudioside A and iso-rebaudioside A along with a large amount of apparently hydrolyzed material corresponding to the loss of one or more sugar moieties (e.g., iso-stevioside, iso-rebaudioside B, iso-rubusoside, iso-steviolbioside, iso-steviolmonoside, etc.).

The glassy oil was dissolved in water (3 mL) and separated by semi-preparative HPLC (Alltech Alltima C-18 semi-preparative column, 10×250 mm, flow rate 5 mL/min, solvent composition 30% acetonitrile in water with 0.1% formic acid). Repeated injections, 15 in all, were made and a peak eluting at 13.7 minutes was collected, the fractions pooled and concentrated to a white powder (23 mg of isolated and purified iso-rebaudioside A). The white powder was first suspended in water (2 mL) and centrifuged. The residual solid was dissolved in warm acetonitrile (200 µL) followed by the addition of water (200 µL) and allowed to sit at room temperature for 5 days whereupon crystals in the form of large needles slowly appeared. The mixture was submitted for x-ray crystallography without perturbing the crystals. The crystals were separated from the liquid portion, and the two samples were dried separately under high vacuum for three days. The dried crystals were used to obtain X-ray crystallography data.

Figure 14:
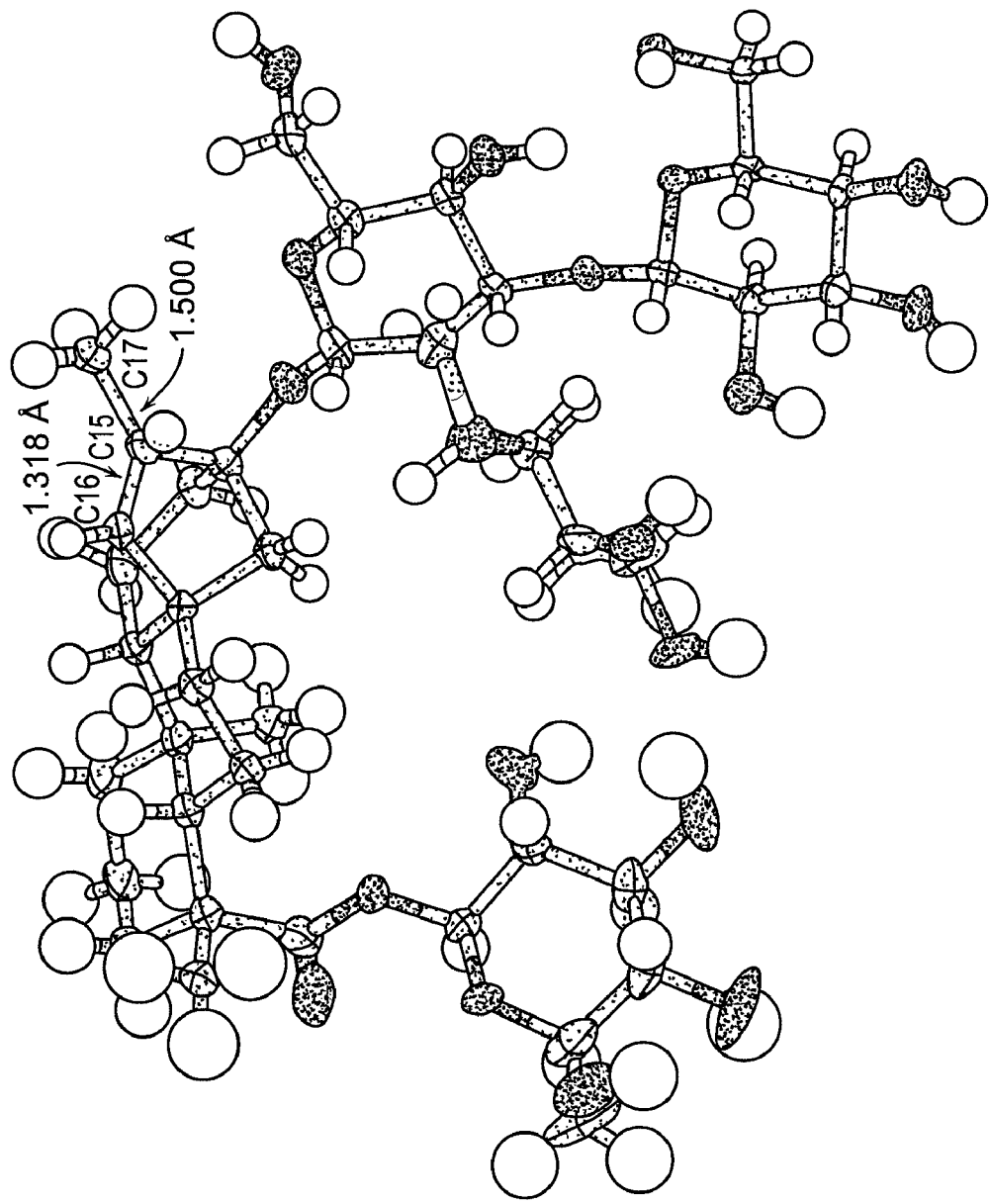
FIG. 14 is an x-ray crystal structure of iso-rebaudioside A
Figure 15:
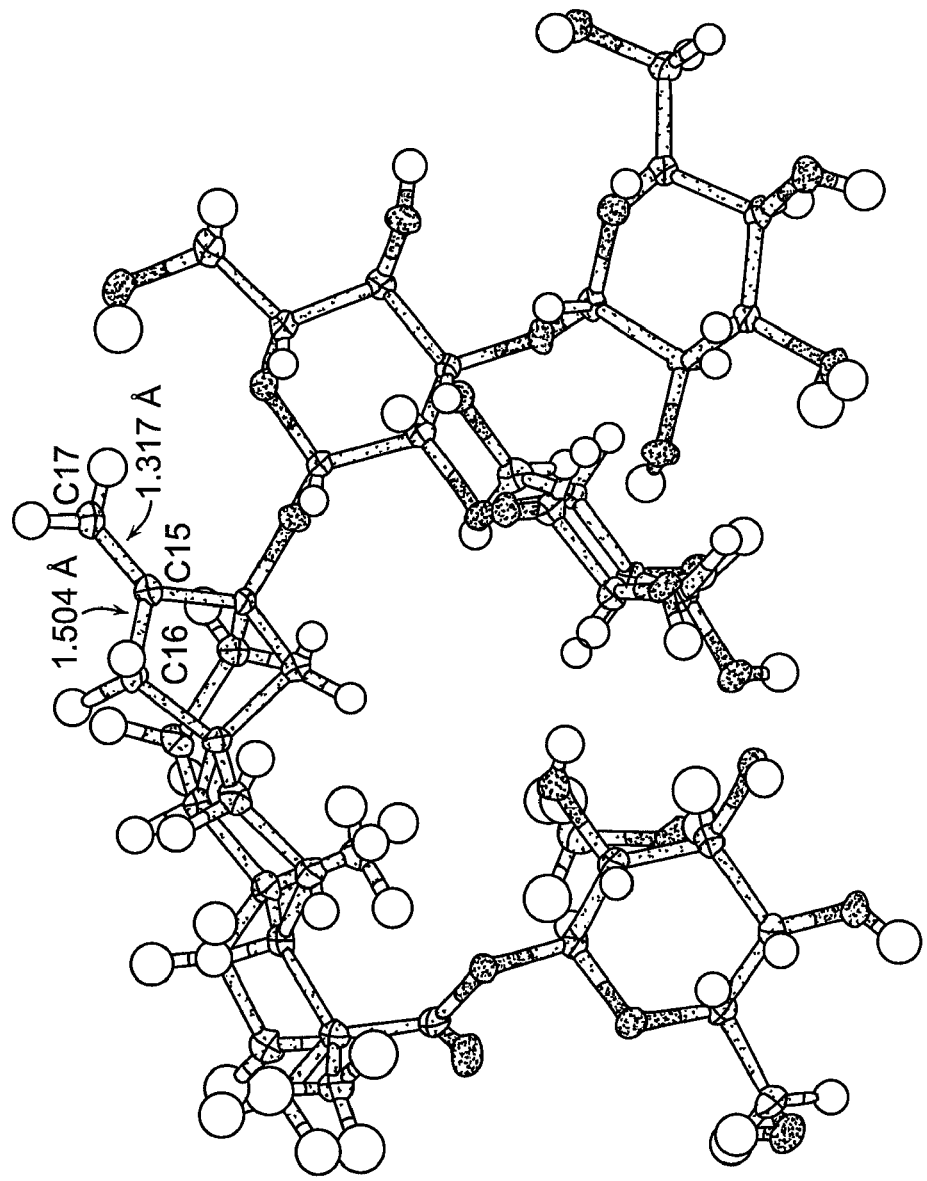
FIG. 15 is an x-ray crystal structure of rebaudioside A
Figure 16:
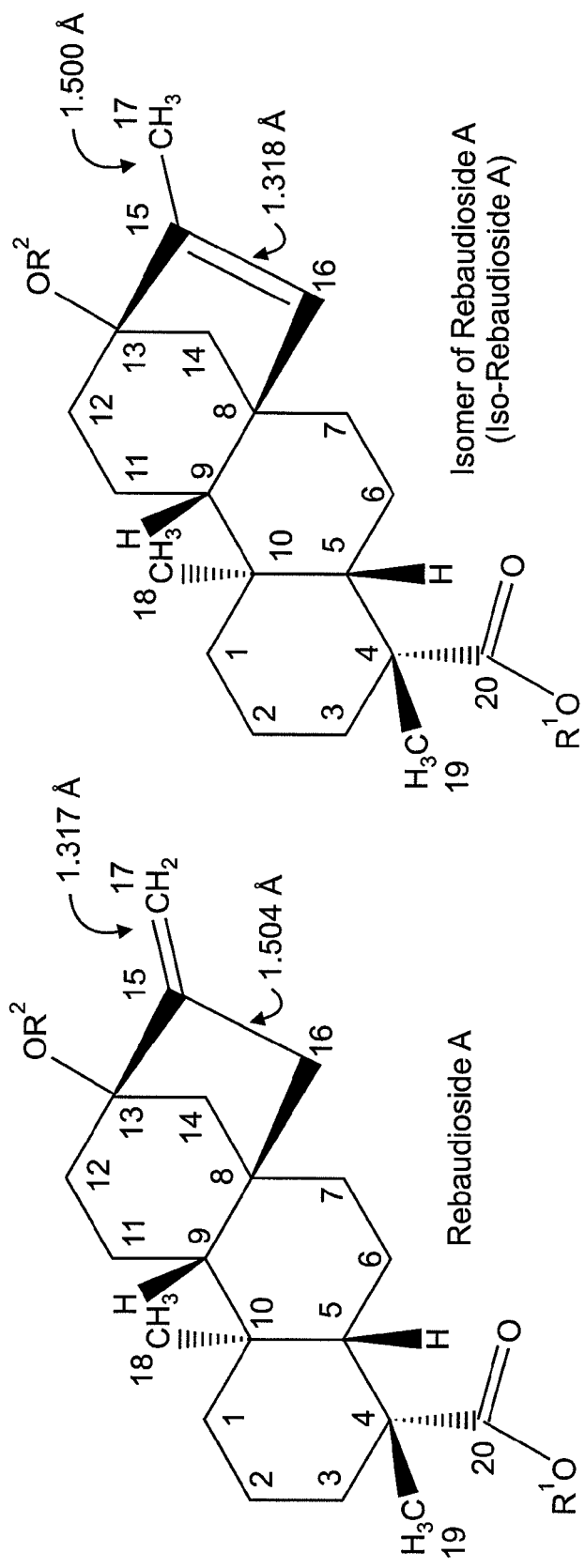
FIG. 16 is a comparison of the structures of rebaudioside A and iso-rebaudioside A

An x-ray crystal structure of iso-rebaudioside A was obtained and the structure was elucidated (see FIG. 14). For comparison, an x-ray crystal structure was obtained for rebaudioside A standard, and the structure was elucidated (FIG. 15). X-ray crystallography analysis unexpectedly showed that the three-dimensional structure of iso-rebaudioside A has an endocyclic double bond in the five-membered ring, with an external methyl group, as evidenced by the shorter bond length between carbons 15 and 16. The crystal structure of rebaudioside A showed the expected exocyclic double bond, as evidenced by the shorter bond length between carbons 15 and 17. See FIG. 16 for a comparison of bond lengths. So surprisingly, the structure of iso-rebaudioside A was shown to be a product of acid-catalyzed double bond migration, and not a product of Wagner-Meerwein rearrangement as predicted based on literature reports wherein under heat and acidic conditions steviol was converted to isosteviol.

Example 4

Iso-rebaudioside A from the x-ray crystallography sample of Example 3 was dissolved in water at a concentration of 1000 ppm, and was found by a panel of five people to have a sweetness intensity similar to that of a 7% sucrose solution; therefore its sweetness potency was estimated to be 70 times that of sucrose.

Example 5

Six reactions were set up under identical conditions as in Example 3 except for temperatures: 43° C., 65° C., 75° C., 85° C., and 90° C. reactions were set up and followed by HPLC-MS or UV (210 nm) detection. It was observed that at elevated temperatures extensive hydrolysis occurred with the largest part of rebaudioside A being hydrolyzed, removing one or more sugar moieties as determined by HPLC-MS analysis as the reaction proceeded.

Example 6

Figure 17:
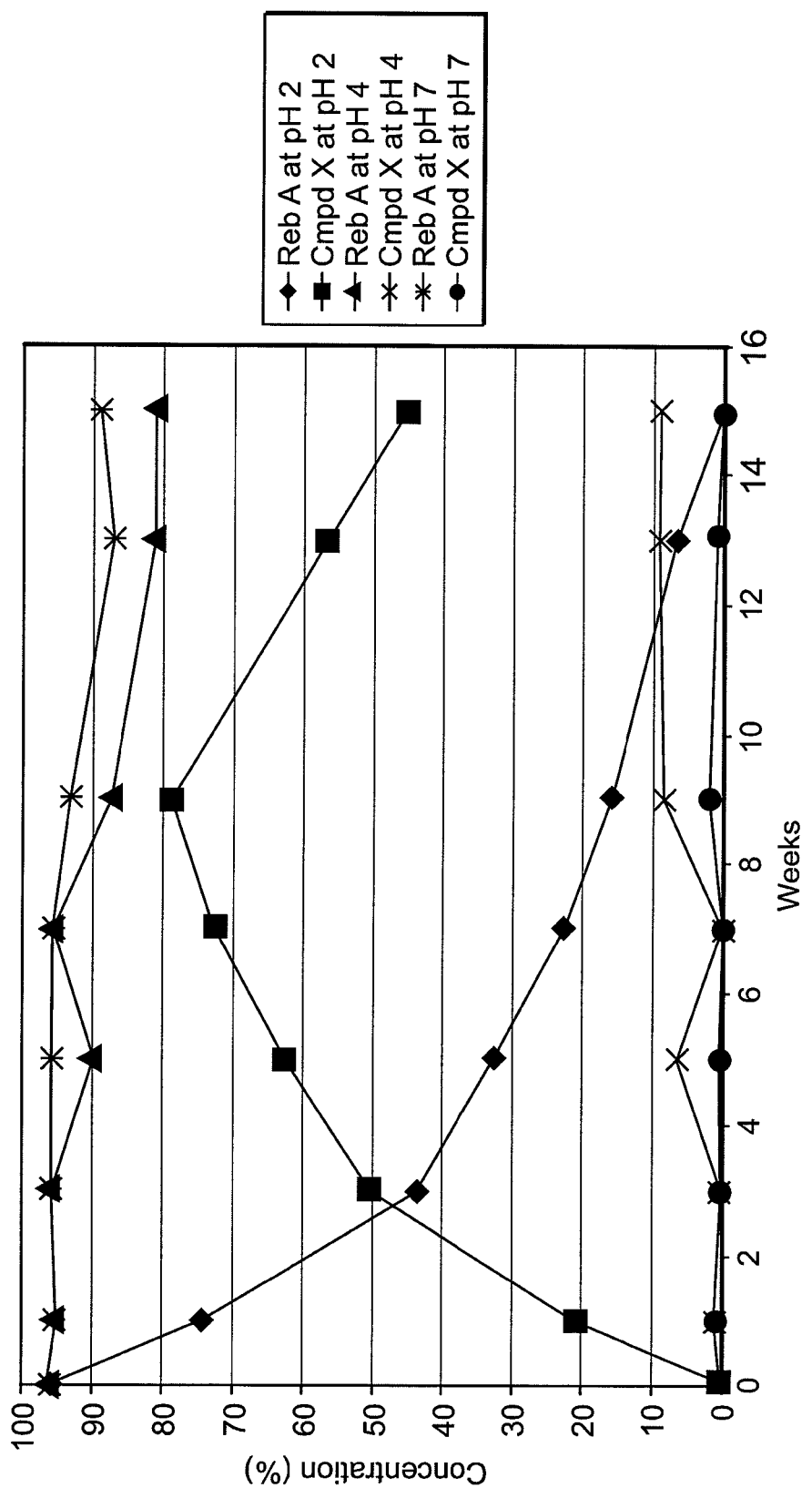
FIGS. 17 and 18 show the pH dependency of the rate of iso-rebaudioside A (Cmpd X) synthesis from rebaudioside A (Reb A).
Figure 18:
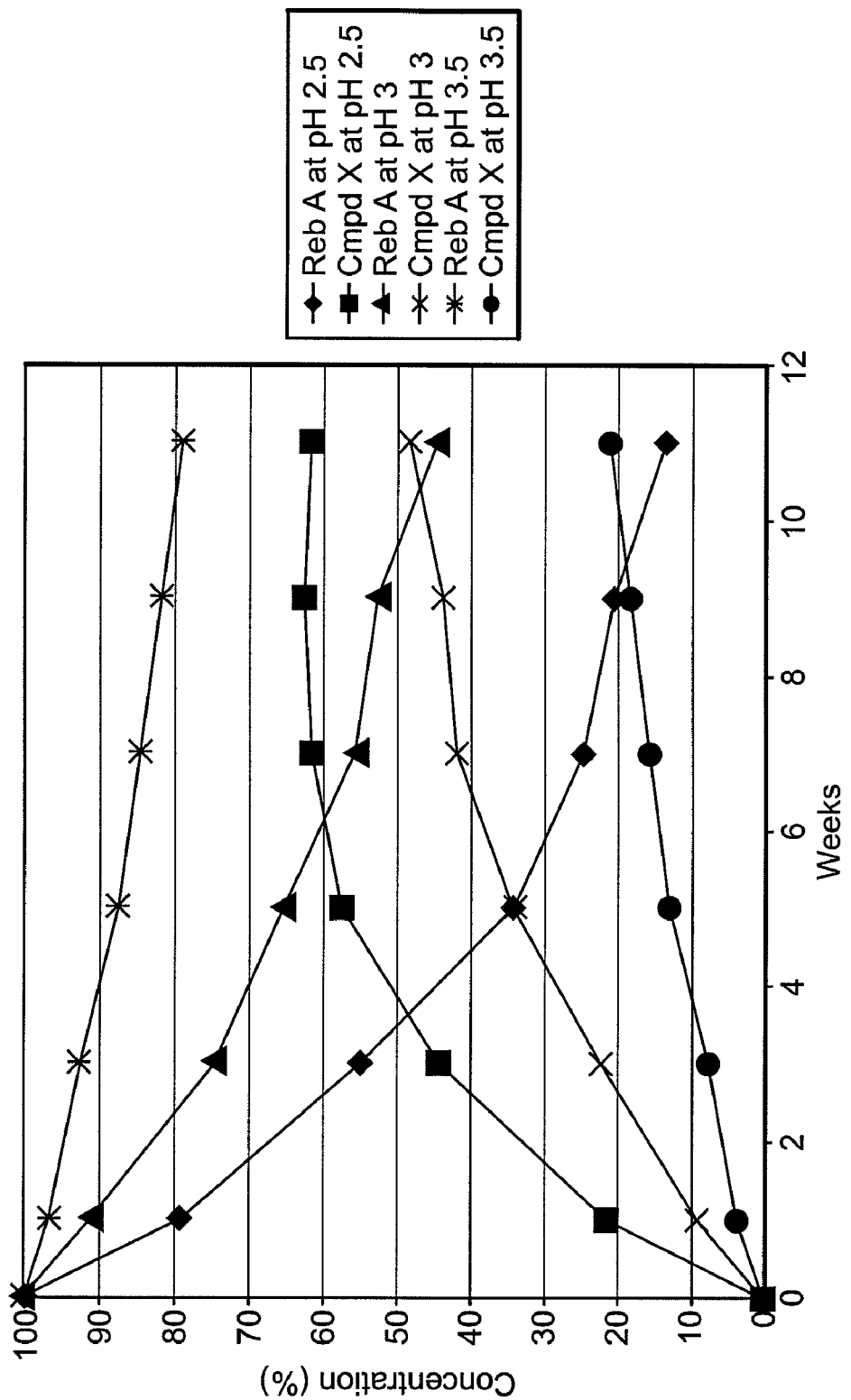

Two studies were performed on the pH dependency of the synthesis of iso-rebaudioside A (Cmpd X) from rebaudioside A (Reb A). Rebaudioside A was dissolved at the same concentration in a series of aqueous citric acid solutions, each having a different pH. The solutions were heated to 43° C. for 11 weeks. One study was performed with solutions at pH 2.0, 4.0, and 7.0. The other study was performed with solutions at pH 2.5, 3.0, and 3.5. Results of the two studies are shown in FIGS. 17 and 18, respectively, wherein Reb A stands for rebaudioside A and Cmpd X stands for iso-rebaudioside A. In FIG. 17, the concentration of iso-rebaudioside A at pH 2 peaks at week 9 and decreases afterwards. The concentration of rebaudioside A at pH 2 continues to decrease after week 9. This indicates that iso-rebaudioside A itself is being degraded/hydrolyzed into other steviol glycoside isomers, e.g. iso-rebaudioside B, etc.

Example 7

Figure 19:
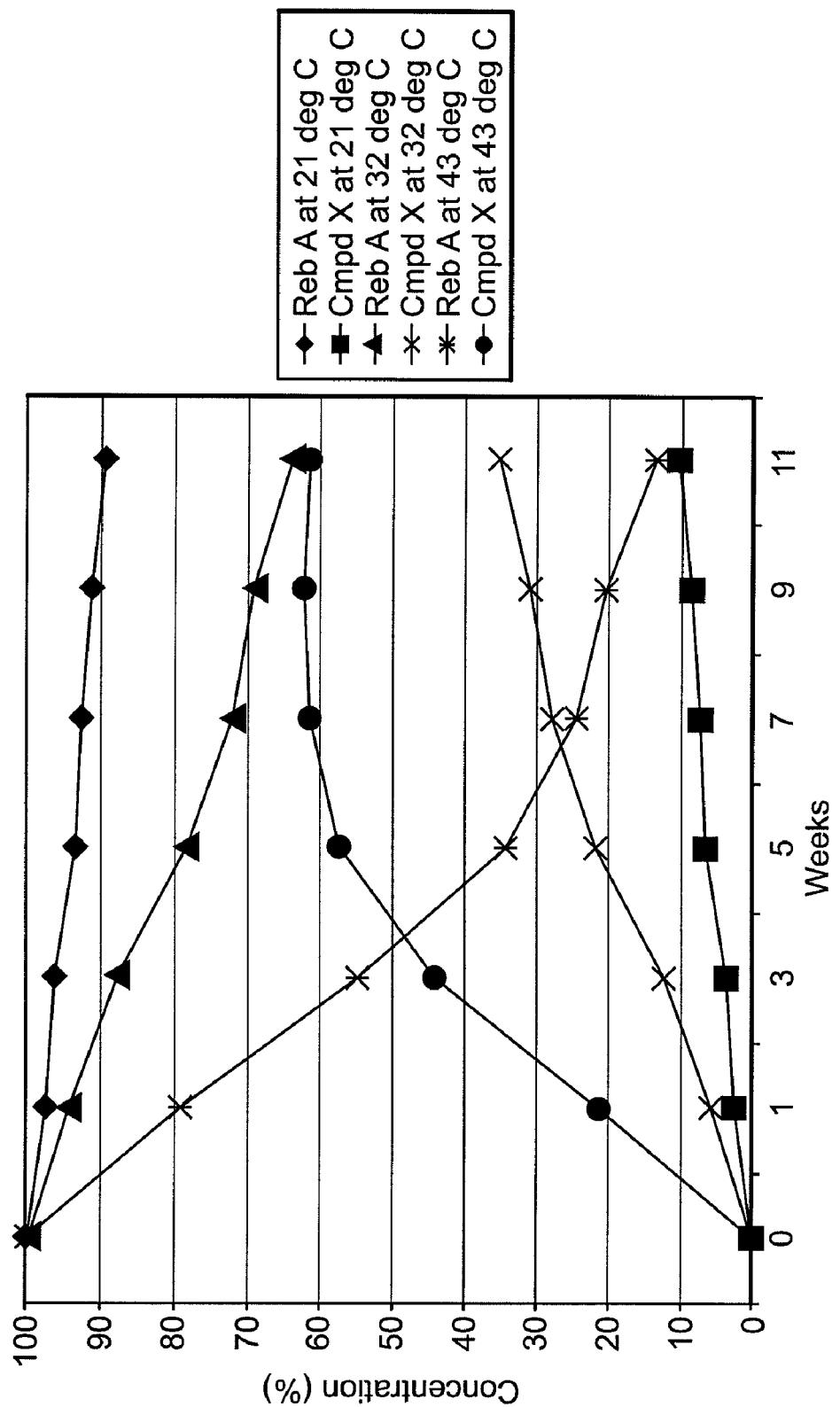
FIG. 19 shows the temperature dependency of the rate of iso-rebaudioside A (Cmpd X) synthesis from rebaudioside A (Reb A).

A study was performed on the temperature dependency of the synthesis of iso-rebaudioside A (Cmpd X) from rebaudioside A (Reb A). Rebaudioside A was dissolved at the same concentration in a series of aqueous citric acid solutions, all at pH 2.5. Each of the solutions was kept at a different temperature (21° C., 32° C., and 43° C.) for 11 weeks. Results of the study are shown in FIG. 19.

The invention has been described with reference to the preferred embodiments. Obviously, modifications and alterations will occur to those skilled in the art upon reading and understanding the preceding detailed description. It is intended that the invention be construed as including all such modifications and alterations insofar as they come within the scope of the appended claims or the equivalents thereof.

What is claimed is:
1. A method for preparing a compound of formula II:

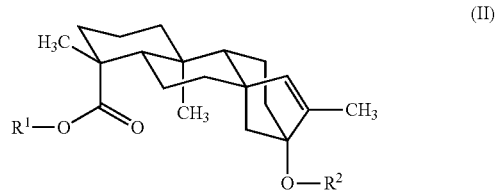

(II)

wherein $R^1$ is 1-β-D-glucopyranosyl, or 2-(1-β-D-glucopyranosyl)-1-β-D-glucopyranosyl, and $R^2$ is hydrogen, 1-β-D-glucopyranosyl, 2-(1-β-D-glucopyranosyl)-1-β-D-glucopyranosyl, 2,3-bis(1-β-D-glucopyranosyl)-1-β-D-glucopyranosyl, 2-(1-α-L-rhamnopyranosyl)-1-β-D-glucopyranosyl, 2-(1-α-L-rhamnopyranosyl)-3-(1-β-D-glucopyranosyl)-1-β-D-glucopyranosyl, or 2-(1-β-D-xylopyranosyl)-3-(1-β-D-glucopyranosyl)-1-β-D-glucopyranosyl, comprising the steps of:
providing an acidic aqueous solution comprising a compound of formula I:

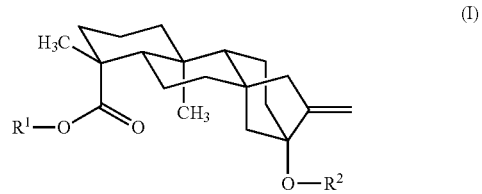

(I)

wherein $R^1$ is 1-β-D-glucopyranosyl or 2-(1-β-D-glucopyranosyl)-1-β-D-glucopyranosyl, and $R^2$ is hydrogen, 1-β-D-glucopyranosyl, 2-(1-β-D-glucopyranosyl)-1-β-D-glucopyranosyl, 2,3-bis(1-β-D-glucopyranosyl)-1-β-D-glucopyranosyl, 2-(1-α-L-rhamnopyranosyl)-1-β-D- glucopyranosyl, 2-(1-α-L-rhamnopyranosyl)-3-(1-β-D-glucopyranosyl)-1-β-D-glucopyranosyl, or 2-(1-β-D-xylopyranosyl)-3-(1-β-D-glucopyranosyl)-1-β-D-glucopyranosyl; and heating the solution to a temperature within the range of 30° C. to 90° C. for a period of time greater than two days.

2. The method of claim 1, wherein $R^1$ is 1-β-D-glucopyranosyl and $R^2$ is 2,3-bis(1-β-D-glucopyranosyl)-1-β-D-glucopyranosyl in the compound of formula I.

3. The method of claim 1, wherein the temperature is within the range of 40° C. to 50° C., and the acidic aqueous solution further comprises at least one of phosphoric acid, hydrochloric acid, nitric acid, sulfuric acid, citric acid, malic acid, tartaric acid, lactic acid, and ascorbic acid, in an amount sufficient to achieve a pH value within the range of pH 1.0-4.0.

4. The method of claim 3, wherein the acidic aqueous solution has a pH value within the range of pH 2.0-2.5.

5. The method of claim 4, wherein the period of time is from 2 days to 11 weeks.

6. The method of claim 1, wherein the acidic aqueous solution further has a pH value within the range of pH 2.0-2.5.

7. The method of claim 1, wherein $R^1$ of Formula II is 1-β-D-glucopyranosyl and $R^2$ of Formula II is 2-(1-β-D-glucopyranosyl)-1-β-D-glucopyranosyl.

8. The method of claim 1, wherein $R^1$ of Formula II is 2-(1-β-D-glucopyranosyl)-1-β-D-glucopyranosyl and $R^2$ of Formula II is 2,3-bis(1-β-D-glucopyranosyl)-1-β-D-glucopyranosyl.

9. The method of claim 1, wherein $R^1$ of Formula II is 2-(1-β-D-glucopyranosyl)-1-β-D-glucopyranosyl and $R^2$ of Formula II is 2-(1-β-D-glucopyranosyl)-1-β-D-glucopyranosyl.

10. The method of claim 1, wherein $R^1$ of Formula II is 1-β-D-glucopyranosyl and $R^2$ of Formula II is 1-β-D-glucopyranosyl.

11. The method of claim 1, wherein $R^1$ of Formula II is 1-β-D-glucopyranosyl and $R^2$ of Formula II is 2-(1-β-D-xylopyranosyl)-3-(1-β-D-glucopyranosyl)-1-β-D-glucopyranosyl.

12. The method of claim 1, wherein $R^1$ of Formula II is 1-β-D-glucopyranosyl and $R^2$ of Formula II is hydrogen.

13. The method of claim 1, wherein $R^1$ of Formula II is 1-β-D-glucopyranosyl and $R^2$ of Formula II is 2-(1-α-L-rhamnopyranosyl)-1-β-D-glucopyranosyl.

14. The method of claim 1, wherein $R^1$ of Formula II is 1-β-D-glucopyranosyl and $R^2$ of Formula II is 2-(1-α-L-rhamnopyranosyl)-3-(1-β-D-glucopyranosyl)-1-β-D-glucopyranosyl.

15. The method of claim 1, wherein $R^1$ of Formula II is 2-(1-β-D-glucopyranosyl)-1-β-D-glucopyranosyl, and $R^2$ of Formula II is hydrogen.

16. The method of claim 1, wherein $R^1$ of Formula II is 2-(1-β-D-glucopyranosyl)-1-β-D-glucopyranosyl, and $R^2$ of Formula II is 1-β-D-glucopyranosyl.

17. The method of claim 1, wherein $R^1$ of Formula II is 2-β-D-glucopyranosyl)-1-β-D-glucopyranosyl, and $R^2$ of Formula II is 2-(1-α-L-rhamnopyranosyl)-1-β-D-glucopyranosyl.

18. The method of claim 1, wherein $R^1$ of Formula II is 2-(1-β-D-glucopyranosyl)-1-β-D-glucopyranosyl, and $R^2$ of Formula II is 2-(1-α-L-rhamnopyranosyl)-3-(1-β-D-glucopyranosyl)-1-β-D-glucopyranosyl.

19. The method of claim 1, wherein $R^1$ of Formula II is 2-(1-β-D-glucopyranosyl)-1-β-D-glucopyranosyl, and $R^2$ of Formula II is 2-(1-β-D-xylopyranosyl)-3-(1-β-D-glucopyranosyl)-1-β-D-glucopyranosyl.

20. The method of claim 1, wherein at least 1.0% by weight of the compound of formula I is converted to the compound of formula II.

* * * * *